(12) United States Patent
Ukegawa et al.

(10) Patent No.: US 12,391,652 B2
(45) Date of Patent: Aug. 19, 2025

(54) CRYSTAL OF 3-(DIFLUOROMETHYL)-1-METHYL-N-(1,1,3-TRIMETHYL-2,3-DIHYDRO-1H-INDEN-4-YL)-1H-PYRAZOLE-4- CARBOXAMIDE

(71) Applicant: SUMITOMO CHEMICAL COMPANY, LIMITED, Tokyo (JP)

(72) Inventors: Tomoya Ukegawa, Sunto-Gun (JP); Satoshi Watanabe, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 653 days.

(21) Appl. No.: 17/772,191

(22) PCT Filed: Oct. 21, 2020

(86) PCT No.: PCT/JP2020/039524
§ 371 (c)(1),
(2) Date: Apr. 27, 2022

(87) PCT Pub. No.: WO2021/085263
PCT Pub. Date: May 6, 2021

(65) Prior Publication Data
US 2022/0402878 A1    Dec. 22, 2022

(30) Foreign Application Priority Data

Nov. 1, 2019   (JP) ................. 2019-200115

(51) Int. Cl.
*A01N 43/56*    (2006.01)
*C07D 231/14*   (2006.01)

(52) U.S. Cl.
CPC .......... *C07D 231/14* (2013.01); *A01N 43/56* (2013.01); *C07B 2200/13* (2013.01)

(58) Field of Classification Search
CPC ............................ C07D 231/14; A01N 43/56
See application file for complete search history.

(56) References Cited

U.S. PATENT DOCUMENTS

2017/0166532 A1   6/2017   Matsunaga et al.
2017/0253630 A1   9/2017   Omatsu et al.

FOREIGN PATENT DOCUMENTS

| JP | 6-505252 A | 6/1994 | |
|----|------------|--------|---|
| JP | 2015-86163 A | 5/2015 | |
| WO | WO 92/12970 A1 | 8/1992 | |
| WO | WO-2011162397 A1 * | 12/2011 | ............. A01N 43/56 |

(Continued)

OTHER PUBLICATIONS

English translation of International Preliminary Report on Patentability and Written Opinion of the International Searching Authority for International Application No. PCT/JP/2020/039524, dated May 3, 2022.

(Continued)

*Primary Examiner* — Bethany P Barham
*Assistant Examiner* — Danielle D Johnson
(74) *Attorney, Agent, or Firm* — Birch, Stewart, Kolasch & Birch, LLP

(57) ABSTRACT

3-(difluoromethyl)-1-methyl-N-(1,1,3-trimethyl-2,3-dihydro-1H-inden-4-yl)-1H-pyrazole-4-carboxamide, which is selected from at least one of a group consisting of a Ra1 type crystal form, a Ra2 type crystal form, and a Ra3 type crystal form, each of the crystal form has a diffraction peaks described in the Description in a powder x-ray diffraction due to Cu-Kα radiation.

9 Claims, 21 Drawing Sheets

(56) References Cited

FOREIGN PATENT DOCUMENTS

| WO | WO 2014/103812 A1 | 7/2014 |
| WO | WO 2015/118793 A1 | 8/2015 |
| WO | WO 2016/031463 A1 | 3/2016 |

OTHER PUBLICATIONS

English translation of International Search Report for International Application No. PCT/JP/2020/039524, dated Dec. 28, 2020.
Hirayama, "Handbook of Organic Compounds crystallization", cols. 2 .1, 4. 1, 2008, pp. 1-3 (5 pages total), with a partial English translation.
Mori, "Creation of Perfect Protein Crystals", CREST (Core Research for Evolutional Science and Technology), Research Final Report 2010 of JST Strategic Basic Research Programs CREST, 2011, pp. 1-75 (84 pages total), with partial English translation.
Chilean Office Action for Chilean Application No. 202201087, dated Oct. 5, 2023, with English translation.
Chilean Search Report for Chilean Application No. 202201087, dated Oct. 5, 2023, with English translation.
Notification of Examiner's Report for Chilean Application No. 202201087, dated Oct. 5, 2023.
Caira, "Crystalline Polymorphism of Organic Compounds", Topics in Current Chemistry, vol. 198, 1998, pp. 163-208.
Indonesian Office Action for Indonesian Application No. P00202205797, dated Aug. 25, 2023, with an English translation.
Partial Supplementary European Search Report for European Application No. 20882153.8, dated Aug. 22, 2023.
"Evaluation Report concerning the composition of the agricultural body of the Ininvert Fluchi," Japan Institute of Agriculture, Agricultural Division (fourth), Feb. 15, 2019.
Japanese Office Action for Japanese Application No. 2021-553488, dated Sep. 17, 2024, with an English translation.
Extended European Search Report for corresponding European Application No. 20882153.8, dated Nov. 23, 2023.
Indian Office Action for corresponding Indian Application No. 202247030025, dated Nov. 29, 2023, with English translation.
Gruzdez, "Chemical Protection of Plants," 1987, pp. 1, 12-16 and 386-389 (10 pages total).
Hirayama, "Handbook of Organic Compounds crystallization," 2008, pp. 17-23, 37-40, 45-51, and 57-65 (29 pages total).
Japanese Office Action for Japanese Application No. 2021-553488, dated May 7, 2024, with English translation.
Russian Office Action and Search Report for Russian Application No. 2022114437, dated Feb. 21, 2024, with English translation.
Sarma et al., "Solid forms of pharmaceuticals: Polymorphs, salts and cocrystals," Korean J. Chem. Eng., vol. 28, No. 2, 2011, pp. 315-322 (pp. 315-317, 3 pages total).
Variankaval et al., "From Form to Function: Crystallization of Active Pharmaceutical Ingredients," AlChE Journal, vol. 54, No. 7, Jul. 2008, pp. 1682-1688.
Chinese Office Action and Search Report for Chinese Application No. 202080076190.9, dated Jun. 25, 2024, with an English translation.
Wang Yu, "Thermal Analysis and Drug Analysis," China Medical Science and Technology Press, First Edition, Jun. 2015, p. 96, with an English translation.
Matskevich et al., "Soviet Encyclopedia," Publishing House, Moscow, 1969, 15 pages total, with an English translation.

* cited by examiner

CRYSTAL OF 3-(DIFLUOROMETHYL)-1-METHYL-N-(1,1,3-TRIMETHYL-2,3-DIHYDRO-1H-INDEN-4-YL)-1H-PYRAZOLE-4-CARBOXAMIDE

TECHNICAL FIELD

The present invention relates to a novel crystal of 3-(difluoromethyl)-1-methyl-N-(1,1,3-trimethyl-2,3-dihydro-1H-inden-4-yl)-1H-pyrazole-4-carboxamide having a plant disease controlling efficacy.

BACKGROUND ART

Hitherto, it has been reported that 3-(difluoromethyl)-1-methyl-N-(1,1,3-trimethyl-2,3-dihydro-1H-inden-4-yl)-1H-pyrazole-4-carboxamide (hereinafter, referred to as "Compound A") is a crystal having a melting point of 131 to 134° C., and showing a control efficacy against plant diseases (see Patent Literature 1).
Patent Literature 1: WO 92/12970 pamphlet

DISCLOSURE OF INVENTION

Technical Problem

An object of the present invention is to provide a novel crystal which has different physical properties than those of a publicly known crystal described in the Patent Literature 1 (hereinafter, the crystal is referred to as "Ra4 type crystal form") and also shows more excellent control efficacy against plant diseases.

Technical Solution

The present inventors have found out three kinds of novel crystals of the Compound A ("Ra1 type crystal form", "Ra2 type crystal form", and "Ra3 type crystal form"), each having an excellent control efficacy against plant diseases.

That, the present invention provides the following embodiments.

[1] A crystal of 3-(difluoromethyl)-1-methyl-N-(1,1,3-trimethyl-2,3-dihydro-1H-inden-4-yl)-1H-pyrazole-4-carboxamide, which is selected from at least one of a group consisting of
   a Ra1 type crystal form which in a powder x-ray diffraction due to Cu-Kα radiation, has a diffraction peaks 2θ of 7.1±0.2°, 8.6±0.2°, 8.9±0.2°, 9.1±0.2°, 13.3±0.2°, 14.0±0.2°, 14.3±0.2°, 14.8±0.2°, 16.0±0.2°, 16.4±0.2°, 20.3±0.2°, and 20.6±0.2°,
   a Ra2 type crystal form which in a powder x-ray diffraction due to Cu-Kα radiation, has a diffraction peaks 2θ of 4.3±0.2°, 8.5±0.2°, 10.8±0.2°, 11.4±0.2°, 12.4±0.2°, 12.8±0.2°, 15.1±0.2°, 16.1±0.2°, 16.8±0.2°, and 19.1±0.2°, and
   a Ra3 type crystal form which in a powder x-ray diffraction due to Cu-Kα radiation, has a diffraction peaks 2θ of 3.6±0.2°, 7.1±0.2°, 7.4±0.2°, 9.6±0.2°, 11.9±0.2°, 12.5±0.2°, 12.9±0.2°, 14.3±0.2°, 15.7±0.2°, and 17.9±0.2°.

[2] The crystal of 3-(difluoromethyl)-1-methyl-N-(1,1,3-trimethyl-2,3-dihydro-1H-inden-4-yl)-1H-pyrazole-4-carboxamide according to [1], which is a Ra1 type crystal form which in a powder x-ray diffraction due to Cu-Kα radiation, has a diffraction peaks 2θ of 7.1±0.2°, 8.6±0.2°, 8.9±0.2°, 9.1±0.2°, 13.3±0.2°, 14.0±0.2°, 14.3±0.2°, 14.8±0.2°, 16.0±0.2°, 16.4±0.2°, 20.3±0.2°, and 20.6±0.2°.

[3] The crystal of 3-(difluoromethyl)-1-methyl-N-(1,1,3-trimethyl-2,3-dihydro-1H-inden-4-yl)-1H-pyrazole-4-carboxamide according to [1], which is a Ra2 type crystal form which in a powder x-ray diffraction due to Cu-Kα radiation, has a diffraction peaks 2θ of 4.3±0.2°, 8.5±0.2°, 10.8±0.2°, 11.4±0.2°, 12.4±0.2°, 12.8±0.2°, 15.1±0.2°, 16.1±0.2°, 16.8±0.2°, and 19.1±0.2°.

[4] The crystal of 3-(difluoromethyl)-1-methyl-N-(1,1,3-trimethyl-2,3-dihydro-1H-inden-4-yl)-1H-pyrazole-4-carboxamide according to [1], which is a Ra3 type crystal form which in a powder x-ray diffraction due to Cu-Kα radiation, has a diffraction peaks 2θ of 3.6±0.2°, 7.1±0.2°, 7.4±0.2°, 9.6±0.2°, 11.9±0.2°, 12.5±0.2°, 12.9±0.2°, 14.3±0.2°, 15.7±0.2°, and 17.9±0.2°.

[5] A composition for controlling a plant disease comprising one or more crystals according to any one of [1] to [4].

[6] A method for controlling a plant disease which comprises applying an effective amount of one or more crystals according to any one of [1] to [4] to a plant or a soil where the plant grows.

[7] Use of one or more crystal according to any one of [1] to [4] for controlling a plant disease.

[8] A composition which comprises one or more ingredients selected from the group consisting of the following Groups (a), (b), (c) and (d), as well as one or more crystals according to any one of [1] to [4]:
   Group (a): a group consisting of insecticidal ingredients, miticidal ingredients, and nematicidal ingredients;
   Group (b): fungicidal ingredients;
   Group (c): plant growth modulating ingredients; and
   Group (d): repellent ingredients.

[9] A seed or vegetative reproductive organ carrying an effective amount of one or more crystal according to any one of [1] to [4] or an effective amount of the composition according to [7].

Effect of Invention

The present invention provides three kinds of novel crystals of the compound A showing a control efficacy against plant diseases (that is, a Ra1 type crystal form, a Ra2 type crystal form, and a Ra3 type crystal form). These crystals can show superior control efficacy against plant diseases compared to a publicly known Ra4 type crystal form.

MODE FOR CARRYING OUT THE INVENTION

Figure 1:
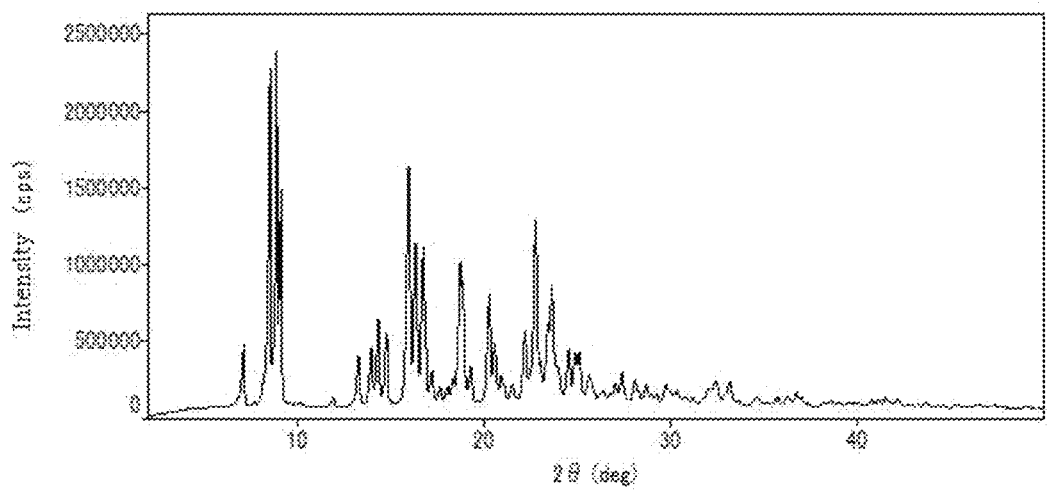
FIG. 1 is a figure showing powder x-ray diffraction patterns of Ra1 type crystal form. The vertical axis represents diffraction intensity (unit: cps) and the horizontal axis represents diffraction angle (2θ) (unit: °).

The present invention relates to novel crystals of the compound A (that is, the Ra1 type crystal form, the Ra2 type crystal form, and the Ra3 type crystal form). The 3-(difluoromethyl)-1-methyl-N-(1,1,3-trimethyl-2,3-dihydro-1H-inden-4-yl)-1H-pyrazole-4-carboxamide is a compound encompassing two kinds of enantiomers such as R form and S form, and the compound A is a mixture composed of each equivalent amount of thereof, that is, a racemate. Also, the crystal in which each equal amount of the R form and the S form are arranged with a regularity in a crystal lattice represents a crystal of the present invention, which makes depending on the process condition, the Ra1 type crystal form, the Ra2 type crystal form, or the Ra3 type crystal form, respectively.

The Ra4 type crystal form has a melting point of about 131 to 134° C., and in a powder x-ray diffraction due to Cu-Kα radiation, has a diffraction peak values 2θ (°) of 5.8±0.2, 7.2±0.2, 8.6±0.2, 13.8±0.2, 16.3±0.2, 16.7±0.2, 17.4±0.2, 17.7±0.2, 19.4±0.2, 19.8±0.2, and 20.7±0.2.

The Ra1 type crystal form, the Ra2 type crystal form, and the Ra3 type crystal form has the following physical property respectively.

The Ra1 type crystal form is a crystal which has a melting point of about 134 to 136° C., and in a powder x-ray diffraction due to Cu-Kα radiation, has a diffraction peak values 2θ (°) of 7.1±0.2, 8.6±0.2, 8.9±0.2, 9.1±0.2, 13.3±0.2, 14.0±0.2, 14.3±0.2, 14.8±0.2, 16.0±0.2, 16.4±0.2, 20.3±0.2, and 20.6±0.2.

The Ra1 type crystal form can be prepared according to the below-mentioned process.

The required amount (for example, about 200 mg) of the Ra2 type crystal form is heated at about 130° C. for a certain time (about 2 hours) in an appropriate container (for example, 20 mL sample bottle) to obtain the Ra1 type crystal form.

The Ra2 type crystal form is a crystal which has a melting point of about 124 to 126° C., and in a powder x-ray diffraction due to Cu-Kα radiation, has a diffraction peak values 2θ (°) of 4.3±0.2, 8.5±0.2, 10.8±0.2, 11.4±0.2, 12.4±0.2, 12.8±0.2, 15.1±0.2, 16.1±0.2, 16.8±0.2, and 19.1±0.2.

The Ra2 type crystal form can be prepared according to the below-mentioned process.

The required amount (for example, about 30 mg) of the compound A is dissolved in an appropriate amount (about 80 μL) of organic solvents (for example, methanol) at about 60° C. to adjust the solution to be a certain amount of a dissolution concentration (about 375 mg/mL). After the solution is cooled to room temperature, a laser is irradiated to the solution under a certain condition, and the solution is allowed to stand at about 20° C. to obtain the Ra2 type crystal form.

The laser irradiation condition may include below, and should not be limited thereto.

<Femtosecond Laser>
 wavelength: 800 nm
 pulse width: 181 fs
 number of pulse: 125 pulses/10 seconds Examples of the organic solvents include alcohol solvents, and include preferably an alkyl solvents containing 1 to 3 carbon atoms. Specific examples thereof include methanol, ethanol, propanol, and isopropanol, and preferably methanol.

The amounts of the organic solvent include an amount that achieves a dissolution concentration of about 200 mg/mL to about 1000 mg/mL of the compound A as opposed to the organic solvents to be used at dissolving. The dissolution concentration of the compound A include preferably about 300 mg/L to about 500 mg/mL, and for example, about 375 mg/mL.

The Ra3 type crystal form is a crystal which has a melting point of about 129 to 131° C., and in a powder x-ray diffraction due to Cu-Kα radiation, has a diffraction peak values 2θ (°) of 3.6±0.2, 7.1±0.2, 7.4±0.2, 9.6±0.2, 11.9±0.2, 12.5±0.2, 12.9±0.2, 14.3±0.2, 15.7±0.2, and 17.9±0.2.

The Ra3 type crystal form can be prepared according to the below-mentioned process.

To the required amount (for example, about 100 mg) of the Ra1 type crystal form prepared above, an appropriate amount (for example, about 1 mL) of organic solvent is added, and the resulting suspension was heated s to about 60° C., and then allowed to stir for a certain time (about 2 days) under a certain condition (about 1000 rpm), and thereafter, the solvents were removed to obtain the Ra3 type crystal form.

Examples of the organic solvents include ether solvents, and preferably dialkyl ether solvents containing 1 to 3 carbon atoms. Specific examples thereof include dimethyl ether, diethyl ether, dipropyl ether, and diisopropyl ether, and preferably diisopropyl ether.

The amount of the organic solvent is within a range of 5 to 10 parts by weight, and preferably 6 to 8 parts by weight, as opposed to 1 part by weight of the used Ra1 type crystal form.

The one or more crystals selected from the group consisting of the Ra1 type crystal form, the Ra2 type crystal form and the Ra3 type crystal form may be mixed or combined with one or more kinds of ingredients selected from a group consisting of the following Group (a), Group (b), Group (c), and Group (d) (hereinafter, referred to as Present ingredient).

The above-mentioned mixing or combining represents a use of one or more crystals selected from the group consisting of the Ra1 type crystal form, the Ra2 type crystal form, and the Ra3 type crystal form, and the Present ingredient at the same time, separately or at certain intervals.

When one or more crystals selected from the group consisting of the Ra1 type crystal form, the Ra2 type crystal form, and the Ra3 type crystal form, and the present ingredient are used at the same time, the one or more crystals selected from the group consisting of the Ra1 type crystal form, the Ra2 type crystal form, and the Ra3 type crystal form and the present ingredient may be contained in separate formulations respectively or may be contained in the same one formulation.

One aspect of the present invention is a composition comprising one or more ingredients selected from a group consisting of the following Group (a), Group (b), Group (c), and Group (d) as well as one or more crystals selected from the group consisting of the Ra1 type crystal form, the Ra2 type crystal form, and the Ra3 type crystal form (hereinafter, the composition is referred to as "Present composition" or "Composition of the present invention").

Group (a) is a group consisting of
each active component as Acetylcholinesterase inhibitors (for example, carbamate insecticides, or organophosphorus insecticides), GABA-gated chloride channel blockers (for example, phenylpyrazol insecticides), Sodium channel modulators (for example, pyrethroid insecticides), Nicotinic acetylcholine receptor competitive modulators (for example, neonicotinoid insecticides), Nicotinic acetylcholine receptor allosteric modulators, Glutamatergic chlorine ion channel allosteric modulators (for example, macrolide insecticides), Juvenile hormone mimic, Multisite inhibitors, chordotonal organ TRPV channel modulators, Mites growth inhibitors, Mitochondria ATP biosynthetic enzyme inhibitors, Uncouplers of oxidative phosphorylation, Nicotinic acetylcholine receptor channel blocker (for example, Nereistoxin insecticides), Chitin synthesis inhibitors, Molting inhibitors, Ecdysone receptor agonist, Octopamine receptor agonist, Inhibitors of Mitochondrial electron transport system complex I, II, III and IV, Voltage-dependent sodium channel blockers, Acetyl CoA carboxylase inhibitor, Ryanodine receptor modulator (for example, Diamide insecticides), Chordotonal organ modulators, Microbial pesticides; and the other insecticidal, miticidal or nematicidal active components.

These ingredients are classified as a class based on the action mechanism of IRAC.

Group (b) is a group consisting of
Nucleic acid synthesis inhibitors (for example, Phenylamide fungicides, or Acylamino acid fungicides), cell division and cytoskeleton inhibitors (for example, MBC fungicides), Respiratory inhibitors (for example, QoI fungicides or Qil fungicides), Amino acid synthesis and protein synthesis inhibitors (for example, anilinopyridine fungicides), Signal transduction inhibitors, Lipid synthesis and membrane synthesis inhibitors, sterol biosynthesis inhibitors (for example, DMI fungicides such as triazole), cell wall synthesis inhibitors, Melanin synthesis inhibitors, Plant defense inducers, Other action point contact active fungicides, Microbial fungicides, and the other fungicidal ingredients. These are classified as a class based on the action mechanism of FRAC.

Group (c) is a plant growth modulating ingredient group (including Mycorrhizal fungi, and Root nodule bacteria).

Group (d) is a repellent ingredient group consisting of a bird repellent ingredient and an insect repellent ingredient.

Examples of the combination of one or more crystals selected from the group consisting of the Ra1 type crystal form, the Ra2 type crystal form, and the Ra3 type crystal form and the Present ingredient are described below. For example, alanycarb+SX represents a combination of alanycarb and SX.

The symbol of "SX" represents the Ra1 type crystal form, the Ra2 type crystal form, or the Ra3 type crystal form (hereinafter, referred to a "Present crystal or Present crystal form", or "Crystal of the present invention" or "Crystal form of the present invention"). Also, all of the below-mentioned present active component are known ingredients, and are commercially available or may be produced by the known method. If the present ingredient is a microorganism, it is available from the International Depositary Authority. The numerical number in bracket represents a CAS RN (Register Trademark).

Combination of the Present ingredient of the above Group (a) and the Present crystal:

abamectin+SX, acephate+SX, acequinocyl+SX, acetamiprid+SX, acetoprole+SX, acrinathrin+SX, acynonapyr+SX, afidopyropen+SX, afoxolaner+SX, alanycarb+SX, aldicarb+SX, allethrin+SX, alpha-cypermethrin+SX, alpha-endosulfan+SX, aluminium phosphide+SX, amitraz+SX, azadirachtin+SX, azamethiphos+SX, azinphos-ethyl+SX, azinphos-methyl+SX, axocyclotin+SX, bark of *Celastrus angulatus*+SX, bendiocarb+SX, benfluthrin+SX, benfuracarb+SX, bensultap+SX, benzoximate+SX, benzpyrimoxan+SX, beta-cyfluthrin+SX, beta-cypermethrin+SX, bifenazate+SX, bifenthrin+SX, bioallethrin+SX, bioresmethrin+SX, bistrifluron+SX, borax+SX, boric acid+SX, broflanilide+SX, bromopropylate+SX, buprofezin+SX, butocarboxim+SX, butoxycarboxim+SX, cadusafos+SX, calcium phosphide+SX, carbaryl+SX, carbofuran+SX, carbosulfan+SX, cartap hydrochloride+SX, cartap+SX, chinomethionat+SX, chlorantraniliprole+SX, chlordane+SX, chlorethoxyfos+SX, chlorfenapyr+SX, chlorfenvinphos+SX, chlorfluazuron+SX, chlormephos+SX, chloropicrin+SX, chlorpyrifos+SX, chlorpyrifos-methyl+SX, chromafenozide+SX, clofentezine+SX, clothianidin+SX, concanamycin A+SX, coumaphos+SX, cryolite+SX, cyanophos+SX, cyantraniliprole+SX, cycloniliprole+SX, cycloprothrin+SX, cycloxaprid+SX, cyenopyrafen+SX, cyflumetofen+SX, cyfluthrin+SX, cyhalodiamide+SX, cyhalothrin+SX, cyhexatin+SX, cypermethrin+SX, cyphenothrin+SX, cyromazine+SX, dazomet+SX, deltamethrin+SX, demeton-S-methyl+SX, diafenthiuron+SX, diazinon+SX, dichlorvos+SX, dicloromezotiaz+SX, dicofol+SX, dicrotophos+SX, diflovidazin+SX, diflubenzuron+SX, dimefluthrin+SX, dimethoate+SX, dimethylvinphos+SX, dimpropyridaz+SX, dinotefuran+SX, disodium octaborate+SX, disulfoton+SX, DNOC(2-methyl-4,6-dinitrophenol)+SX, doramectin+SX, dried leaves of Dryopteris filix-mas+SX, emamectin-benzoate+SX, empenthrin+SX, endosulfan+SX, EPN(O-ethyl O-(4-nitrophenyl)phenylphosphonothioate)+SX, epsilon-metofluthrin+SX, epsilon-momfluorothrin+SX, esfenvalerate+SX, ethiofencarb+SX, ethion+SX, ethiprole+SX, ethoprophos+SX, etofenprox+SX, etoxazole+SX, extract of *Artemisia absinthium*+SX, extract of *Cassia nigricans*+SX, extract of clitoria ternatea+SX, extract of *Symphytum officinale*+SX, extracts or simulated blend of *Chenopodium ambrosioides*+SX, extract of *Tanacetum vulgare*+SX, extract of *Urtica dioica*+SX, extract of Viscum album+SX, famphur+SX, fenamiphos+SX, fenazaquin+SX, fenbutatin oxide+SX, fenitrothion+SX, fenobucarb+SX, fenoxycarb+SX, fenpropathrin+SX, fenpyroximate+SX, fenthion+SX, fenvalerate+SX, fipronil+SX, flometoquin+SX, flonicamid+SX, fluacrypyrim+SX, fluazaindolizine+SX, fluazuron+SX, flubendiamide+SX, flucycloxuron+SX, flucythrinate+SX, fluensulfone+SX, flufenoprox+SX, flufenoxuron+SX, flufiprole+SX, flumethrin+SX, flupyradifurone+SX, flupyrimin+SX, fluralaner+SX, fluvalinate+SX, fluxametamide+SX, formetanate+SX, fosthiazate+SX, furamethrin+SX, furathiocarb+SX, gamma-cyhalothrin+SX, GS-omega/kappa HXTX-Hv1a peptide+SX, halfenprox+SX, halofenozide+SX, heptafluthrin+SX, heptenophos+SX, hexaflumuron+SX, hexythiazox+SX, potassium salt of hop beta acid+SX, hydramethylnon+SX, hydroprene+SX, imicyafos+SX, imidacloprid+SX, imidaclothiz+SX, imiprothrin+SX, indoxacarb+SX, isocycloseram+SX, isofenphos+SX, isoprocarb+SX, isopropyl-O-(methoxyaminothiophosphoryl) salicylate+SX, isoxathion+SX, ivermectin+SX, kadethrin+SX, kappa-tefluthrin+SX, kappa-bifenthrin+SX, kinoprene+SX, lambda-cyhalothrin+SX, lenoremycin+SX, lepimectin+SX, lime sulfur+SX, lotilaner+SX, lufenuron+SX, machine oil+SX, malathion+SX, mecarbam+SX, meperfluthrin+SX, metaflumizone+SX, metam+SX, methamidophos+SX, methidathion+SX, methiocarb+SX, methomyl+SX, methoprene+SX, methoxychlor+SX, methoxyfenozide+SX, methyl bromide+SX, metofluthrin+SX, metolcarb+SX, metoxadiazone+SX, mevinphos+SX, milbemectin+SX, milbemycin oxime+SX, momfluorothrin+SX, monocrotophos+SX, moxidectin+SX, naled+SX, neem oil+SX, nicotine+SX, nicotine-sulfate+SX, nitenpyram+SX, novaluron+SX, noviflumuron+SX, oil of the seeds of *Chenopodium anthelminticum*+SX, omethoate+SX, oxamyl+SX, oxazosulfyl+SX, oxydemeton-methyl+SX, parathion+SX, parathion-methyl+SX, permethrin+SX, phenothrin+SX, phenthoate+SX, phorate+SX, phosalone+SX, phosmet+SX, phosphamidon+SX, phosphine+SX, phoxim+SX, pirimicarb+SX, pirimiphos-methyl+SX, prallethrin+SX, profenofos+SX, profluthrin+SX, propargite+SX, propetamphos+SX, propoxur+SX, propylene glycol alginate+SX, prothiofos+SX, pyflubumide+SX, pymetrozine+SX, pyraclofos+SX, pyrethrins+SX, pyridaben+SX, pyridalyl+SX, pyridaphenthion+SX, pyrifluquinazone+SX, pyrimidifen+SX, pyriminostrobin+SX, pyriprole+SX, pyriproxyfen+SX, quinalphos+SX, resmethrin+SX, rotenone+SX, ryanodine+SX, sarolaner+SX, selamectin+SX, sigma-cypermethrin+SX, silafluofen+SX, sodium borate+SX, sodium metaborate+SX, spinetoram+SX, spinosad+SX, spirodiclofen+SX, spiromesifen+SX, spiropidion+SX, spirotetramat+SX, sulfluramid+SX, sulfotep+SX, sulfoxaflor+SX, sulfur+SX, sulfuryl fluoride+SX, tartar emetic+SX, tau-fluvalinate+SX, tebufenozide+SX, tebufenpyrad+SX, tebupirimfos+SX, teflubenzuron+SX, tefluthrin+SX, temephos+SX, terbufos+SX, terpene constituents of the extract of *chenopodium ambrosioides* near ambrosioides+SX, tetrachlorantraniliprole+SX, tetrachlorvinphos+SX, tetradifon+SX, tetramethrin+SX, tetramethylfluthrin+SX, tetraniliprole+SX, theta-cypermethrin+SX, thiacloprid+SX, thiamethoxam+SX, thiocyclam+SX, thiodicarb+SX, thiofanox+SX, thiometon+SX, thiosultap-disodium+SX, thiosultap-monosodium+SX, tioxazafen+SX, tolfenpyrad+SX, tralomethrin+SX, transfluthrin+SX, triazamate+SX, triazophos+SX, trichlorfon+SX, triflumezopyrim+SX, triflumuron+SX, trimethacarb+SX, tyclopyrazoflor+SX, vamidothion+SX, wood extract of *Quassia amara*+SX, XMC (3,5-dimethylphenyl N-methylcarbamate)+SX, xylylcarb+SX, zeta-cypermethrin+SX, zinc phosphide+SX, 4-[5-(3,5-dichlorophenyl)-5-(trifluoromethyl)-4,5-dihydro-1,2-oxazol-3-yl]-2-methyl-N-(1-oxothietan-3-yl) benzamide (1241050-20-3)+SX, 3-methoxy-N-(5-{5-(trifluoromethyl)-5-[3-(trifluoromethyl)phenyl]-4,5-dihydro-1,2-oxazol-3-yl}indan-1-yl)propanamide (1118626-57-5)+SX, 2-chloro-4-fluoro-5-{[5-(trifluoromethylthio)pentyl]oxy}phenyl 2,2,2-trifluoroethyl sulfoxide (1472050-04-6)+SX, 4-chloro-5-[2,2-difluoro-2-(3,4,5-trifluorophenyl)ethoxy]-2-methylphenyl 2,2,2-trifluoroethyl sulfoxide (1632218-00-8)+SX, 4-fluoro-5-[2,2-difluoro-2-(3,4,5-trifluorophenyl) ethoxy]-2-methylphenyl 2,2,2-trifluoroethyl sulfoxide (1632217-98-1)+SX, 2-({2-fluoro-4-methyl-5-[(2,2,2-trifluoroethyl)sulfinyl]phenyl}imino)-3-(2,2,2-trifluoroethyl)-1,3-thiazolidin-4-one (1445683-71-5)+SX, (1Z)-2-(4-tert-butylphenyl)-2-cyano-1-(1-ethyl-3-methyl-1H-pyrazol-5-yl)ethenyl 2,2-dimethylpropanoate (1253429-01-4)+SX, N-[(1S,2S)-2-(2,4-dichlorophenyl)cyclobutyl]-2-(trifluoromethyl)pyridine-3-carboxamide (1644251-74-0)+SX, (3R)-3-(2-chlorothiazol-5-yl)-8-methyl-7-oxo-6-phenyl-2,3-dihydrothiazolo[3,2-a]pyrimidin-4-ium-5-olate (2249718-27-0)+SX, BT crop protein Cry1Ab+SX, BT crop protein Cry1Ac+SX, BT crop protein Cry1Fa+SX, BT crop protein Cry1A105+SX, BT crop protein Cry2Ab+SX, BT crop protein Vip3A+SX, BT crop protein Cry3A+SX, BT crop protein Cry3Ab+SX, BT crop protein Cry3Bb+SX, BT crop protein Cry34AB1/Cry35AB1+SX, *Adoxophyes orana* granulosis virus strain BV-0001+SX, *Anticarsia gemmatalis* mNPV+SX, *Autographa californica* mNPV+SX, *Cydia pomonella* GV strain V15+SX, *Cydia pomonella* GV strain V22+SX, Cryptophlebia leucotreta GV+SX, *Dendrolimus* punctatus cypovirus+SX, *Helicoverpa armigera* NPV strain BV-0003+SX, *Helicoverpa zea* NPV+SX, *Lymantria dispar* NPV+SX, *Mamestra brassicae*

NPV+SX, Mamestra configurata NPV+SX, Neodiprion abietis NPV+SX, Neodiprion lecontei NPV+SX, Neodiprion sertifer NPV+SX, Nosema locustae+SX, Orgyia pseudotsugata NPV+SX, Pieris rapae GV+SX, Plodia interpunctella GV+SX, Spodoptera exigua mNPV+SX, Spodoptera littoralis mNPV+SX, Spodoptera litura NPV+SX, Arthrobotrys dactyloides+SX, Bacillus firmus strain GB126+SX, Bacillus firmus strain 1-1582+SX, Bacillus megaterium+SX, Bacillus sp. strain AQ175+SX, Bacillus sp. strain AQ177+SX, Bacillus sp. strain AQ178+SX, Bacillus sphaericus strain 2362+SX, Bacillus sphaericus strain ABTS1743+SX, Bacillus sphaericus Serotype strain H5a5b+SX, Bacillus thuringiensis strain AQ52+SX, Bacillus thuringiensis strain BD #32+SX, Bacillus thuringiensis strain CR371+SX, Bacillus thuringiensis subsp. Aizawai strain ABTS-1857+SX, Bacillus thuringiensis subsp. Aizawai strain AM65-52+SX, Bacillus thuringiensis subsp. Aizawai strain GC-91+SX, Bacillus thuringiensis subsp. Aizawai Serotype strain H-7+SX, Bacillus thuringiensis subsp. Kurstaki strain ABTS351+SX, Bacillus thuringiensis subsp. Kurstaki strain BMP123+SX, Bacillus thuringiensis subsp. Kurstaki strain EG234+SX, Bacillus thuringiensis subsp. Kurstaki strain EG7841+SX, Bacillus thuringiensis subsp. Kurstaki strain EVB113-19+SX, Bacillus thuringiensis subsp. Kurstaki strain F810+SX, Bacillus thuringiensis subsp. Kurstaki strain HD-1+SX, Bacillus thuringiensis subsp. Kurstaki strain PB54+SX, Bacillus thuringiensis subsp. Kurstaki strain SA11+SX, Bacillus thuringiensis subsp. Kurstaki strain SA12+SX, Bacillus thuringiensis subsp. Tenebriosis strain NB176+SX, Bacillus thuringiensis subsp. Thuringiensis strain MPPL002+SX, Bacillus thuringiensis subsp.morrisoni+SX, Bacillus thuringiensis var. colmeri+SX, Bacillus thuringiensis var. darmstadiensis strain 24-91+SX, Bacillus thuringiensis var. dendrolimus+SX, Bacillus thuringiensis var. galleriae+SX, Bacillus thuringiensis var. israelensis strain BMP144+SX, Bacillus thuringiensis var. israelensis serotype strain H-14+SX, Bacillus thuringiensis var. japonensis strain buibui+SX, Bacillus thuringiensis var. san diego strain M-+SX, Bacillus thuringiensis vaR7216+SX, Bacillus thuringiensis var.aegypti+SX, Bacillus thuringiensis var. T36+SX, Beauveria bassiana strain ANT-03+SX, Beauveria bassiana strain ATCC74040+SX, Beauveria bassiana strain GHA+SX, Beauveria brongniartii+SX, Burkholderia rinojensis strain A396+SX, Chromobacterium subtsugae strain PRAA4-1T+SX, Dactyllela ellipsospora+SX, Dectylaria thaumasia+SX, Hirsutella minnesotensis+SX, Hirsutella rhossiliensis+SX, Hirsutella thompsonii+SX, Lagenidium giganteum+SX, Lecanicillium lecanii strain KV01+SX, Lecanicillium lecanii conidia of strain DA0M198499+SX, Lecanicillium lecanii conidia of strain DA0M216596+SX, Lecanicillium muscarium strain Ve6+SX, Metarhizium anisopliae strain F52+SX, Metarhizium anisopliae var. acridum+SX, Metarhizium anisopliae var. anisopliae BIPESCO 5/F52+SX, Metarhizium flavoviride+SX, Monacrosporium phymatopagum+SX, Paecilomyces fumosoroseus Apopka strain 97+SX, Paecilomyces lilacinus strain 251+SX, Paecilomyces tenuipes strain T1+SX, Paenibacillus popilliae+SX, Pasteuria nishizawae strain Pn1+SX, Pasteuria penetrans+SX, Pasteuria usgae+SX, Pasteuria thoynei+SX, Serratia entomophila+SX, Verticillium chlamydosporium+SX, Verticillium lecani strain NCIM1312+SX, 2-chloro-N-cyclopropyl-5-{1-[2,6-dichloro-4-(1,1,1,2,3,3,3-heptafluoropropan-2-yl)phenyl]-1H-pyrazol-4-yl}-N-methylpyridine-3-carboxamide (1771741-86-6)+SX, N-{4-chloro-3-[(1-cyanocyclopropyl)carbamoyl]phenyl}-1-methyl-4-(methanesulfonyl)-3-(1,1,2,2,2-pentafluoroethyl)-1H-pyrazole-3-carboxamide (1400768-21-9)+SX, 11-(4-chloro-2,6-dimethylphenyl)-12-hydroxy-1,4-dioxa-9-azadispiro[4.2.4.2]tetradec-11-en-10-one (907187-07-9)+SX, 3-(4'-fluoro-2,4-dimethyl[1,1'-biphenyl]-3-yl)-4-hydroxy-8-oxa-1-azaspiro[4.5]dec-3-en-2-one (1031385-91-7)+SX, N-[3-chloro-1-(pyridin-3-yl)-1H-pyrazol-4-yl]-2-(methanesulfonyl)propanamide (2396747-83-2)+SX, 2-isopropyl-5-[(3,4,4-trifluoro-3-buten-1-yl)sulfonyl]-1,3,4-thiadiazole (2058052-95-0)+SX, 1,4-dimethyl-2-[2-(3-pyridinyl)-2H-indazol-5-yl]-1,2,4-triazolidine-3,5-dione (2171099-09-3)+SX, and cyproflanilide+SX.

Combination of the Present ingredient of the above Group (b) and the Present crystal:

acibenzolar-S-methyl+SX, aldimorph+SX, ametoctradin+SX, aminopyrifen+SX, amisulbrom+SX, anilazine+SX, azaconazole+SX, azoxystrobin+SX, basic copper sulfate+SX, benalaxyl+SX, benalaxyl-M+SX, benodanil+SX, benomyl+SX, benthiavalicarb+SX, benthivalicarb-isopropyl+SX, benzovindiflupyr+SX, binapacryl+SX, biphenyl+SX, bitertanol+SX, bixafen+SX, blasticidin-S+SX, Bordeaux mixture+SX, boscalid+SX, bromothalonil+SX, bromuconazole+SX, bupirimate+SX, captafol+SX, captan+SX, carbendazim+SX, carboxin+SX, carpropamid+SX, chinomethionat+SX, chitin+SX, chloroneb+SX, chlorothalonil+SX, chlozolinate+SX, colletochlorin B+SX, copper(II) acetate+SX, copper(II) hydroxide+SX, copper oxychloride+SX, copper(II) sulfate+SX, coumoxystrobin+SX, cyazofamid+SX, cyflufenamid+SX, cymoxanil+SX, cyproconazole+SX, cyprodinil+SX, dichlobentiazox+SX, dichlofluanid+SX, diclocymet+SX, diclomezine+SX, dicloran+SX, diethofencarb+SX, difenoconazole+SX, diflumetorim+SX, dimethachlone+SX, dimethirimol+SX, dimethomorph+SX, dimoxystrobin+SX, diniconazole+SX, diniconazole-M+SX, dinocap+SX, dipotassium hydrogenphosphite+SX, dipymetitrone+SX, dithianon+SX, dodecylbenzenesulphonic acid bisethylenediamine copper(II) salt+SX, dodemorph+SX, dodine+SX, edifenphos+SX, enoxastrobin+SX, epoxiconazole+SX, etaconazole+SX, ethaboxam+SX, ethirimol+SX, etridiazole+SX, extract from Melaleuca alternifolia+SX, extract from Reynoutria sachalinensis+SX, extract from the cotyledons of lupine plantlets("BLAD")+SX, extract of Allium sativum+SX, extract of Equisetum arvense+SX, extract of Tropaeolum majus+SX, famoxadone+SX, fenamidone+SX, fenaminstrobin+SX, fenarimol+SX, fenbuconazole+SX, fenfuram+SX, fenhexamid+SX, fenoxanil+SX, fenpiclonil+SX, fenpicoxamid+SX, fenpropidin+SX, fenpropimorph+SX, fenpyrazamine+SX, fentin acetate+SX, fentin chloride+SX, fentin hydroxide+SX, ferbam+SX, ferimzone+SX, florylpicoxamid+SX, fluazinam+SX, fludioxonil+SX, flufenoxystrobin+SX, fluindapyr+SX, flumorph+SX, fluopicolide+SX, fluopyram+SX, fluopimomide+SX, fluoroimide+SX, fluoxapiprolin+SX, fluoxastrobin+SX, fluquinconazole+SX, flusilazole+SX, flusulfamide+SX, flutianil+SX, flutolanil+SX, flutriafol+SX, fluxapyroxad+SX, folpet+SX, fosetyl+SX, fosetyl-aluminium+SX, fuberidazole+SX, furalaxyl+SX, furametpyr+SX, guazatine+SX, hexaconazole+SX, hymexazole+SX, imazalil+SX, imibenconazole+SX, iminoctadine+SX, iminoctadine triacetate+SX, inpyrfluxam+SX, iodocarb+SX, ipconazole+SX, ipfentrifluconazole+SX, ipflufenoquin+SX, iprobenfos+SX, iprodione+SX, iprovalicarb+SX, isofetamid+SX, isoflucypram+SX, isoprothiolane+SX, isopyrazam+SX, isotianil+SX, kasugamycin+SX, kresoxim-methyl+SX, laminarin+SX, leaves and bark of *Quercus*+SX, mancozeb+SX, mandestrobin+SX, mandipropamid+SX, maneb+SX, mefentrifluconazole+SX, mepanipyrim+SX, mepronil+SX, meptyldinocap+SX, metalaxyl+SX, metalaxyl-M+SX, metconazole+SX, methasulfocarb+SX, metiram+SX, metominostrobin+SX, metrafenone+SX, metyltetraprole+SX, mineral oils+SX, myclobutanil+SX, naftifine+SX, nuarimol+SX, octhilinone+SX, ofurace+SX, orysastrobin+SX, oxadixyl+SX, oxathiapiprolin+SX, oxine-copper+SX, oxolinic acid+SX, oxpoconazole+SX, oxpoconazole fumarate+SX, oxycarboxin+SX, oxytetracycline+SX, pefurazoate+SX, penconazole+SX, pencycuron+SX, penflufen+SX, penthiopyrad+SX, phenamacril+SX, phosphorous acid+SX, phthalide+SX, picarbutrazox+SX, picoxystrobin+SX, piperalin+SX, polyoxins+SX, potassium hydrogencarbonate+SX, potassium dihydrogenphosphite+SX, probenazole+SX, prochloraz+SX, procymidone+SX, propamidine+SX, propamocarb+SX, propiconazole+SX, propineb+SX, proquinazid+SX, prothiocarb+SX, prothioconazole+SX, pydiflumetofen+SX, pyraclostrobin+SX, pyrametostrobin+SX, pyraoxystrobin+SX, pyrapropoyne+SX, pyraziflumid+SX, pyrazophos+SX, pyribencarb+SX, pyributicarb+SX, pyridachlometyl+SX, pyrifenox+SX, pyrimethanil+SX, pyrimorph+SX, pyriofenone+SX, pyrisoxazole+SX, pyroquilon+SX, *Quillaja extract*+SX, quinconazole+SX, quinofumelin+SX, quinoxyfen+SX, quintozene+SX, Saponins of *Chenopodium quinoa*+SX, sedaxane+SX, silthiofam+SX, simeconazole+SX, sodium hydrogencarbonate+SX, spiroxamine+SX, streptomycin+SX, sulfur+SX, tebuconazole+SX, tebufloquin+SX, teclofthalam+SX, tecnazene+SX, terbinafine+SX, tetraconazole+SX, thiabendazole+SX, thifluzamide+SX, thiophanate+SX, thiophanate-methyl+SX, thiram+SX, thymol+SX, tiadinil+SX, tolclofos-methyl+SX, tolfenpyrad+SX, tolprocarb+SX, tolylfluanid+SX, triadimefon+SX, triadimenol+SX, triazoxide+SX, triclopyricarb+SX, tricyclazole+SX, tridemorph+SX, trifloxystrobin+SX, triflumizole+SX, triforine+SX, triticonazole+SX, validamycin+SX, valifenalate+SX, vinclozolin+SX, yellow mustard powder+SX, zinc thiazole+SX, zineb+SX, ziram+SX, zoxamide+SX, N'-[4-({3-[(4-chlorophenyl)methyl]-1,2,4-thiadiazol-5-yl}oxy)-2,5-dimethylphenyl]-N-ethyl-N-methylmethanimidamide (1202781-91-6)+SX, N'-{4-[(4,5-dichlorothiazol-2-yl)oxy]-2,5-dimethylphenyl}-N-ethyl-N-methylmethanimidamide (929908-57-6)+SX, N'-(2,5-dimethyl-4-phenoxyphenyl)-N-ethyl-N-methylmethanimidamide (1052688-31-9)+SX, N'-[5-choro-4-(2-fluorophenoxy)-2-methylphenyl)-N-ethyl-N-methylmethanimidamide (2055589-28-9)+SX, N'-[2-choro-4-(2-fluorophenoxy)-5-methylphenyl)-N-ethyl-N-methylmethanimidamide (2055756-21-1)+SX, N'-[4-(1-hydroxy-1-phenyl-2,2,2-trifluoroethyl)-2-methyl-5-methoxyphenyl)-N-isopropyl-N-methylmethanimidamide (2101814-55-3)+SX, N'-[5-bromo-6-(1-methyl-2-propoxyethoxy)-2-methylpyridin-3-yl)-N-ethyl-N-methylmethanimidamide (1817828-69-5)+SX, 4-(2-bromo-4-fluorophenyl)-N-(2-chloro-6-fluorophenyl)-1,3-dimethyl-1H-pyrazol-5-amine (1362477-26-6)+SX, 2-[6-(3-fluoro-4-methoxyphenyl)-5-methylpyridin-2-yl]quinazoline (1257056-97-5)+SX, 5-fluoro-4-imino-3-methyl-1-tosyl-3,4-dihydropyrimidin-2(1H)-one (1616664-98-2)+SX, ethyl (2Z)-3-amino-2-cyano-3-phenylacrylate (39491-78-6)+SX, N-[(2-chlorothiazol-5-yl)methyl]-N-ethyl-6-methoxy-3-nitropyridin-2-amine (1446247-98-8)+SX, 5-(4-chlorobenzyl)-2-(chloromethyl)-2-methyl-1-(1H-1,2,4-triazol-1-ylmethyl)cyclopentan-1-ol (1394057-11-4)+SX, (1R, 2S, 5S)-5-(4-chlorobenzyl)-2-(chloromethyl)-2-methyl-1-(1H-1,2,4-triazol-1-ylmethyl)cyclopentan-1-ol (1801930-06-2)+SX, (1S, 2R, 5R)-5-(4-chlorobenzyl)-2-(chloromethyl)-2-methyl-1-(1H-1,2,4-triazol-1-ylmethyl)cyclopentan-1-ol (1801930-07-3)+SX, 2-(chloromethyl)-5-(4-fluorobenzyl)-2-methyl-1-(1H-1,2,4-triazol-1-ylmethyl)cyclopentan-1-ol (1394057-13-6)+SX, (1R, 2S, 5S)-2-(chloromethyl)-5-(4-fluorobenzyl)-2-methyl-1-(1H-1,2,4-triazol-1-ylmethyl)cyclopentan-1-ol (1801930-08-4)+SX, (1S, 2R, 5R)-2-(chloromethyl)-5-(4-fluorobenzyl)-2-methyl-1-(1H-1,2,4-triazol-1-ylmethyl)cyclopentan-1-ol (1801930-09-5)+SX, methyl 3-[(4-chlorophenyl)methyl]-2-hydroxy-1-methyl-2-(1H-1,2,4-triazol-1-ylmethyl)cyclopentan-1-carboxylate (1791398-02-1)+SX, 1-(2,4-difluorophenyl)-2-(1H-1,2,4-triazol-1-yl)-1-[1-(4-bromo-2,6-difluorophenoxy)cyclopropyl]ethanol (2019215-86-0)+SX, 1-(2,4-difluorophenyl)-2-(1H-1,2,4-triazol-1-yl)-1-[1-(4-chloro-2,6-difluorophenoxy)cyclopropyl]ethanol (2019215-84-8)+SX, 1-[2-(1-chlorocyclopropyl)-3-(2-fluorophenyl)-2-hydroxypropyl]-1H-imidazole-5-carbonitrile (2018316-13-5)+SX, 1-[2-(1-chlorocyclopropyl)-3-(2,3-difluorophenyl)-2-hydroxypropyl]-1H-imidazole-5-carbonitrile (2018317-25-2)+SX, 4-({6-[2-(2,4-difluorophenyl)-1,1-difluoro-2-hydroxy-3-(1H-1,2,4-triazol-1-yl)propyl]pyridin-3-yl}oxy)benzonitrile (2046300-61-0)+SX, 2-[6-(4-bromophenoxy)-2-(trifluoromethyl)pyridin-3-yl]-1-(1H-1,2,4-triazol-1-yl)propan-2-ol (2082661-43-4)+SX, 2-[6-(4-chlorophenoxy)-2-(trifluoromethyl)pyridin-3-yl]-1-(1H-1,2,4-triazol-1-yl)propan-2-ol (2082660-27-1)+SX, methyl ({2-methyl-5-[1-(4-methoxy-2-methylphenyl)-1H-pyrazol-3-yl]phenyl}methyl)carbamate (1605879-98-8)+SX, 2-(difluoromethyl)-N-[1,1,3-trimethyl-2,3-dihydro-1H-inden-4-yl]pyridine-3-carboxamide (1616239-21-4)+SX, 2-(difluoromethyl)-N-[3-ethyl-1,1-dimethyl-2,3-dihydro-1H-inden-4-yl]pyridine-3-carboxamide (1847460-02-9)+SX, 2-(difluoromethyl)-N-β-propyl-1,1-dimethyl-2,3-dihydro-1H-inden-4-yl]pyridine-3-carboxamide (1847460-05-2)+SX, (2E,3Z)-5-{[1-(4-chlorophenyl)-1H-pyrazol-3-yl]oxy}-2-(methoxyimino)-N,3-dimethylpent-3-enamide (1445331-27-0)+SX, (2E,3Z)-5-{[1-(2,4-dichlorophenyl)-1H-pyrazol-3-yl]oxy}-2-(methoxyimino)-N,3-dimethylpent-3-enamide (1445331-54-3)+SX, 5-chloro-4-({2-[6-(4-chlorophenoxy)pyridin-3-yl]ethyl}amino)-6-methylpyrimidine (1605340-92-8)+SX, N-(1-benzyl-1,3-dimethylbutyl)-8-fluoroquinoline-3-carboxamide (2132414-04-9)+SX, N-(1-benzyl-3,3,3-trifluoro-1-methylpropyl)-8-fluoroquinoline-3-carboxamide (2132414-00-5)+SX, 4,4-dimethyl-2-({4-[5-(trifluoromethyl)-1,2,4-oxadiazol-3-yl]phenyl}methyl)isoxazolidin-3-one (2098918-25-1)+

SX, 5,5-dimethyl-2-({4-[5-(trifluoromethyl)-1,2,4-oxadiazol-3-yl]phenyl}methyl)isoxazolidin-3-one (2098918-26-2)+SX, *Agrobacterium radiobactor* strain K1026+SX, *Agrobacterium radiobactor* strain K84+SX, *Bacillus amyloliquefaciens* (Aveo(Trade mark) EZ Nematicide)+SX, *Bacillus amyloliquefaciens* strain AT332+SX, *Bacillus amyloliquefaciens* strain B3+SX, *Bacillus amyloliquefaciens* strain D747+SX, *Bacillus amyloliquefaciens* strain DB101+SX, *Bacillus amyloliquefaciens* strain DB102+SX, *Bacillus amyloliquefaciens* strain GB03+SX, *Bacillus amyloliquefaciens* strain FZB24+SX, *Bacillus amyloliquefaciens* strain FZB42+SX, *Bacillus amyloliquefaciens* strain IN937a+SX, *Bacillus amyloliquefaciens* strain MBI600+SX, *Bacillus amyloliquefaciens* strain QST713+SX, *Bacillus amyloliquefaciens* isolate strain B246+SX, *Bacillus amyloliquefaciens* strain F727+SX, *Bacillus amyloliquefaciens* subsp. *plantarum* strain D747+SX, *Bacillus licheniformis* strain HB-2+SX, *Bacillus licheniformis* strain SB3086+SX, *Bacillus pumilus* strain AQ717+SX, *Bacillus pumilus* strain BUF-33+SX, *Bacillus pumilus* strain GB34+SX, *Bacillus pumilus* strain QST2808+SX, *Bacillus simplex* strain CGF2856+SX, *Bacillus subtilis* strain AQ153+SX, *Bacillus subtilis* strain AQ743+SX, *Bacillus subtilis* strain BU1814+SX, *Bacillus subtilis* strain D747+SX, *Bacillus subtilis* strain DB101+SX, *Bacillus subtilis* strain FZB24+SX, *Bacillus subtilis* strain GB03+SX, *Bacillus subtilis* strain HAI0404+SX, *Bacillus subtilis* strain IAB/BS03+SX, *Bacillus subtilis* strain MBI600+SX, *Bacillus subtilis* strain QST30002/AQ30002+SX, *Bacillus subtilis* strain QST30004/AQ30004+SX, *Bacillus subtilis* strain QST713+SX, *Bacillus subtilis* strain QST714+SX, *Bacillus subtilis* var. *Amyloliquefaciens* strain FZB24+SX, *Bacillus subtilis* strain Y1336+SX, *Burkholderia cepacia*+SX, *Burkholderia cepacia* type Wisconsin strain J82+SX, *Burkholderia cepacia* type Wisconsin strain M54+SX, *Candida oleophila* strain O+SX, *Candida saitoana*+SX, *Chaetomium cupreum*+SX, *Clonostachys rosea*+SX, *Coniothyrium minitans* strain CGMCC8325+SX, *Coniothyrium minitans* strain CON/M/91-8+SX, *cryptococcus albidus*+SX, *Erwinia carotovora* subsp. *carotovora* strain CGE234M403+SX, *Fusarium oxysporum* strain Fo47+SX, *Gliocladium catenulatum* strain J1446+SX, *Paenibacillus polymyxa* strain AC-1+SX, *Paenibacillus polymyxa* strain BS-0105+SX, *Pantoea agglomerans* strain E325+SX, *Phlebiopsis gigantea* strain VRA1992+SX, *Pseudomonas aureofaciens* strain TX-1+SX, *Pseudomonas chlororaphis* strain 63-28+SX, *Pseudomonas chlororaphis* strain AFS009+SX, *Pseudomonas chlororaphis* strain MA342+SX, *Pseudomonas fluorescens* strain 1629RS+SX, *Pseudomonas fluorescens* strain A506+SX, *Pseudomonas fluorescens* strain CL145A+SX, *Pseudomonas fluorescens* strain G7090+SX, *Pseudomonas* sp. strain CAB-02+SX, *Pseudomonas syringae* strain 742RS+SX, *Pseudomonas syringae* strain MA-4+SX, *Pseudozyma flocculosa* strain PF-A22UL+SX, *Pseudomonas rhodesiae* strain HAI-0804+SX, *Pythium oligandrum* strain DV74+SX, *Pythium oligandrum* strain M1+SX, *Streptomyces griseoviridis* strain K61+SX, *Streptomyces lydicus* strain WYCD108US+SX, *Streptomyces lydicus* strain WYEC108+SX, *Talaromyces flavus* strain SAY-Y-94-01+SX, *Talaromyces flavus* strain V117b+SX, *Trichoderma asperellum* strain ICC012+SX, *Trichoderma asperellum* SKT-1+SX, *Trichoderma asperellum* strain T25+SX, *Trichoderma asperellum* strain T34+SX, *Trichoderma asperellum* strain TV1+SX, *Trichoderma atroviride* strain CNCM 1-1237+SX, *Trichoderma atroviride* strain LC52+SX, *Trichoderma atroviride* strain IMI 206040+SX, *Trichoderma atroviride* strain SC1+SX, *Trichoderma atroviride* strain SKT-1+SX, *Trichoderma atroviride* strain T11+SX, *Trichoderma gamsii* strain ICC080+SX, *Trichoderma harzianum* strain 21+SX, *Trichoderma harzianum* strain DB104+SX, *Trichoderma harzianum* strain DSM 14944+SX, *Trichoderma harzianum* strain ESALQ-1303+SX, *Trichoderma harzianum* strain ESALQ-1306+SX, *Trichoderma harzianum* strain IIHR-Th-2+SX, *Trichoderma harzianum* strain ITEM908+SX, *Trichoderma harzianum* strain kd+SX, *Trichoderma harzianum* strain MO1+SX, *Trichoderma harzianum* strain SF+SX, *Trichoderma harzianum* strain T22+SX, *Trichoderma harzianum* strain T39+SX, *Trichoderma harzianum* strain T78+SX, *Trichoderma harzianum* strain TH35+SX, *Trichoderma polysporum* strain IMI206039+SX, *trichoderma stromaticum*+SX, *Trichoderma virens* strain G-41+SX, *Trichoderma virens* strain GL-21+SX, *Trichoderma viride*+SX, *Variovorax paradoxus* strain CGF4526+SX, Harpin protein+SX, flubeneteram+SX, N-acetyl-2-(ethanesulfonyl)-N-[2-(methoxycarbonyl)-4-(trifluoromethoxy)phenyl]-4-(trifluoromethyl)benzamide (2043675-28-9)+SX, (2S,3S)-3-(2-methylphenyl)butan-2-yl N-[(3-acetoxy-4-methoxypyridin-2-yl)carbonyl]-L-alaninate (2376210-00-1)+SX, (2S,3S)-3-(4-fluoro-2-methylphenyl)butan-2-yl N-[(3-acetoxy-4-methoxypyridin-2-yl)carbonyl]-L-alaninate+SX, (2S,3S)-3-(4-methoxy-2-methylphenyl)butan-2-yl N-[(3-acetoxy-4-methoxypyridin-2-yl)carbonyl]-L-alaninate+SX, (2S,3S)-3-(2,4-dimethylphenyl)butan-2-yl N-[(3-acetoxy-4-methoxypyridin-2-yl)carbonyl]-L-alaninate (2376209-13-9)+SX, (2S,3S)-3-(2-methylphenyl)butan-2-yl N-({3-[(2-methylpropanoyl)oxy]-4-methoxypyridin-2-yl}carbonyl)-L-alaninate (2376210-02-3)+SX, (2S,3S)-3-(4-fluoro-2-methylphenyl)butan-2-yl N-({3-[(2-methylpropanoyl)oxy]-4-methoxypyridin-2-yl}carbonyl)-L-alaninate+SX, (2S,3S)-3-(4-methoxy-2-methylphenyl)butan-2-yl N-({3-[(2-methylpropanoyl)oxy]-4-methoxypyridin-2-yl}carbonyl)-L-alaninate (2376209-40-2)+SX, (2S,3S)-3-(2,4-dimethylphenyl)butan-2-yl N-({3-[(2-methylpropanoyl)oxy]-4-methoxypyridin-2-yl}carbonyl)-L-alaninate (2376209-15-1)+SX, N'-(2-choro-4-phenoxy-5-methylphenyl)-N-ethyl-N-methylmethanimidamide (2062599-39-5)+SX, (2S,3S)-3-(2-methylphenyl)butan-2-yl N-[(3-hydroxy-4-methoxypyridin-2-yl)carbonyl]-L-alaninate+SX, (2S,3S)-3-(4-fluoro-2-methylphenyl)butan-2-yl N-[(3-hydroxy-4-methoxypyridin-2-yl)carbonyl]-L-alaninate+SX, (2S,3S)-3-(4-methoxy-2-methylphenyl)butan-2-yl N-[(3-hydroxy-4-methoxypyridin-2-yl)carbonyl]-L-alaninate+SX, (2S,3S)-3-(2,4-dimethylphenyl)butan-2-yl N-[(3-hydroxy-4-methoxypyridin-2-yl)carbonyl]-L-alaninate+SX, (2S,3S)-3-(4-fluoro-2-methylphenyl)-4-methylpentan-2-yl N-[(3-acetoxy-4-methoxypyridin-2-yl)carbonyl]-L-alaninate+SX, (2S,3S)-3-(2-fluoro-4-methylphenyl)-4-methylpentan-2-yl N-[(3-acetoxy-4-methoxypyridin-2-yl)carbonyl]-L-alaninate+SX, (2S,3S)-3-(2,4-difluorophenyl)-4-methylpentan-2-yl N-[(3-acetoxy-4-methoxypyridin-2-yl)carbonyl]-L-alaninate+SX, (2S, 3S)-3-(2,4-dimethylphenyl)-4-methylpentan-2-yl N-[(3-acetoxy-4-methoxypyridin-2-yl)carbonyl]-L-alaninate+SX, (2S,3S)-3-(4-fluoro-2-methoxylphenyl)-4-methylpentan-2-yl N-[(3-acetoxy-4-methoxypyridin-2-yl)carbonyl]-L-alaninate+SX, (2S,3S)-3-(4-fluoro-2-methylphenyl)-4-methylpentan-2-yl N-{[3-(acetoxymethoxy)-4-methoxypyridin-2-yl]carbonyl}-L-alaninate+SX, (2S,3S)-3-(2-fluoro-4-methylphenyl)-4-methylpentan-2-yl N-{[3-(acetoxymethoxy)-4-methoxypyridin-2-yl]carbonyl}-L-alaninate+SX, (2S,3S)-3-(2,4-difluorophenyl)-4-methylpentan-2-yl N-{[3-(acetoxymethoxy)-4-methoxypyridin-2-yl]carbonyl}-L-alaninate+SX, (2S,3S)-3-(2,4-dimethylphenyl)-4-methylpentan-2-yl N-{[3-(acetoxymethoxy)-4-methoxypyridin-2-yl]carbonyl}-L-alaninate+SX, (2S,3S)-3-(4-fluoro-2-methoxylphenyl)-4-methylpentan-2-yl N-{[3-(acetoxymethoxy)-4-methoxypyridin-2-yl]carbonyl}-L-alaninate+SX, (2S,3S)-3-(4-fluoro-2-methylphenyl)-4-methylpentan-2-yl N-({3-[(isobutyryloxy)methoxy]-4-methoxypyridin-2-yl}carbonyl)-L-alaninate+SX, (2S,3S)-3-(2-fluoro-4-methylphenyl)-4-methylpentan-2-yl N-({3-[(isobutyryloxy)methoxy]-4-methoxypyridin-2-yl}carbonyl)-L-alaninate+SX, (2S,3S)-3-(2,4-difluorophenyl)-4-methylpentan-2-yl N-({3-[(isobutyryloxy)methoxy]-4-methoxypyridin-2-yl}carbonyl)-L-alaninate+SX, (2S,3S)-3-(2,4-dimethylphenyl)-4-methylpentan-2-yl N-({3-[(isobutyryloxy)methoxy]-4-methoxypyridin-2-yl}carbonyl)-L-alaninate+SX, (2S,3S)-3-(4-fluoro-2-methoxylphenyl)-4-methylpentan-2-yl N-({3-[(isobutyryloxy)methoxy]-4-methoxypyridin-2-yl}carbonyl)-L-alaninate+SX, (2S,3S)-3-(4-fluoro-2-methylphenyl)-4-methylpentan-2-yl N-[(3-hydroxy-4-methoxypyridin-2-yl)carbonyl]-L-alaninate+SX, (2S,3S)-3-(2-fluoro-4-methylphenyl)-4-methylpentan-2-yl N-[(3-hydroxy-4-methoxypyridin-2-yl)carbonyl]-L-alaninate+SX, (2S,3S)-3-(2,4-difluorophenyl)-4-methylpentan-2-yl N-[(3-hydroxy-4-methoxypyridin-2-yl)carbonyl]-L-alaninate+SX, (2S,3S)-3-(2,4-dimethylphenyl)-4-methylpentan-2-yl N-[(3-hydroxy-4-methoxypyridin-2-yl)carbonyl]-L-alaninate+SX, (2S,3S)-3-(4-fluoro-2-methoxylphenyl)-4-methylpentan-2-yl N-[(3-hydroxy-4-methoxypyridin-2-yl)carbonyl]-L-alaninate+SX.

Combination of the Present ingredient of the above Group (c) and the Present crystal:

1-methylcyclopropene+SX, 1,3-diphenylurea+SX, 2,3,5-triiodobenzoic acid+SX, IAA ((1H-indol-3-yl)acetic acid)+SX, IBA (4-(1H-indol-3-yl)butyric acid)+SX, MCPA (2-(4-chloro-2-methylphenoxy)acetic acid)+SX, MCPB (4-(4-chloro-2-methylphenoxy)butyric acid)+SX, 4-CPA (4-chlorophenoxyacetic acid)+SX, 5-aminolevulinic acid hydrochloride+SX, 6-benzylaminopurine+SX, abscisic acid+SX, AVG (aminoethoxyvinylglycine)+SX, ancymidol+SX, butralin+SX, calcium carbonate+SX, calcium chloride+SX, calcium formate+SX, calcium peroxide+SX, calcium polysulfide+SX, calcium sulfate+SX, chlormequat-chloride+SX, chlorpropham+SX, choline chloride+SX, cloprop+SX, cyanamide+SX, cyclanilide+SX, daminozide+SX, decan-1-ol+SX, dichlorprop+SX, dikegulac+SX, dimethipin+SX, diquat+SX, ethephon+SX, ethychlozate+SX, flumetralin+SX, flurprimidol+SX, forchlorfenuron+SX, formononetin+SX, Gibberellin A+SX, Gibberellin A3+SX, inabenfide+SX, Kinetin+SX, lipochitooligosaccharide SP104+SX, maleic hydrazide+SX, mefluidide+SX, mepiquat-chloride+SX, oxidized glutathione+SX, pacrobutrazol+SX, pendimethalin+SX, prohexandione-calcium+SX, prohydrojasmon+SX, pyraflufen-ethyl+SX, sintofen+SX, sodium 1-naphthaleneacetate+SX, sodium cyanate+SX, streptmycin+SX, thidiazuron+SX, triapenthenol+SX, Tribufos+SX, trinexapac-ethyl+SX, uniconazole-P+SX, 2-(naphthalen-1-yl)acetamide+SX, [4-oxo-4-(2-phenylethyl)amino]butyric acid+SX, methyl 5-(trifluoromethyl)benzo[b]thiophene-2-carboxylate+SX, 3-[(6-chloro-4-phenylquinazolin-2-yl)amino]-1-propanol+SX, *Claroideoglomus etunicatum*+SX, *Claroideoglomus claroideum*+SX, *Funneliformis mosseae*+SX, *Gigaspora margarita*+SX, *Gigaspora rosea*+SX, *Glomus aggregatum*+SX, *Glomus deserticola*+SX, *Glomus monosporum*+SX, *Paraglomus brasillianum*+SX, *Rhizophagus clarus*+SX, *Rhizophagus intraradices* RTI-801+SX, *Rhizophagus irregularis* DAOM 197198+SX, *Azorhizobium caulinodans*+SX, *Azospirillum amazonense*+SX, *Azospirillum brasilense* XOH+SX, *Azospirillum brasilense* Ab-V5+SX, *Azospirillum brasilense* Ab-V6+SX, *Azospirillum caulinodans*+SX, *Azospirillum halopraeferens*+SX, *Azospirillum irakense*+SX, *Azospirillum lipoferum*+SX, *Bradyrhizobium elkanii* SEMIA 587+SX, *Bradyrhizobium elkanii* SEMIA 5019+SX, *Bradyrhizobium japonicum* TAll+SX, *Bradyrhizobium japonicum USDA*110+SX, *Bradyrhizobium liaoningense*+SX, *Bradyrhizobium lupini*+SX, *Delftia acidovorans* RAY209+SX, *Mesorhizobium ciceri*+SX, *Mesorhizobium huakii*+SX, *Mesorhizobium loti*+SX, *Rhizobium etli*+SX, *Rhizobium galegae*+SX, *Rhizobium leguminosarum* bv. *Phaseoli*+SX, *Rhizobium leguminosarum* bv. *Trifolii*+SX, *Rhizobium leguminosarum* bv. *Viciae*+SX, *Rhizobium trifolii*+SX, *Rhizobium tropici*+SX, *Sinorhizobium fredii*+SX, *Sinorhizobium meliloti*+SX, Zucchini Yellow Mosaik Virus weak strain+SX.

Combination of the Present ingredient of the above Group (d) and the Present crystal:

anthraquinone+SX, deet+SX, icaridin+SX.

The ratio of the Present crystal to the Present ingredient includes, but not particularly limited thereto, as a ratio by weight (the Present crystal:the Present ingredient) 1,000:1 to 1:1,000, 500:1 to 1:500, 100:1 to 1:100, 50:1, 20:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:20, and 1:50, and the others.

The present crystal may be mixed or combined with chemical fertilizers (for example, ammonium sulfate, ammonium phosphate, ammonium nitrate, urea, or ammonium chloride).

The Present crystal or the present composition can control plant diseases caused by plant pathogenic microorganisms such as fungi, Oomycete, Phytomyxea, and bacteria. Examples of the fungi include Ascomycota, Basidiomycota, Blastocladiomycota, Chytridiomycota, Mucoromycota, and Olpidiomycota. Specific examples of the plant diseases include the followings. The scientific name of plant pathogenic microorganism which causes each disease is shown in parentheses.

Rice Diseases:

blast (*Pyricularia oryzae*), brown spot (*Cochliobolus miyabeanus*), sheath blight (*Rhizoctonia solani*), bakanae disease (*Gibberella fujikuroi*), downy mildew (*Sclerophthora macrospora*), false blast and head blight (*Epicoccum nigrum*), seedling blight (*Trichoderma viride, Rhizopus oryzae*);

Wheat Diseases:
  powdery mildew (*Blumeria graminis*), fusarium blight (*Fusarium graminearum, Fusarium avenaceum, Fusarium culmorum, Microdochium nivale*), stripe rust (*Puccinia striiformis*), stem rust (*Puccinia graminis*), leaf rust (*Puccinia recondita*), snow mould (*Microdochium nivale, Microdochium majus*), typhula snow blight (*Typhula incarnata, Typhula ishikariensis*), loose smut (*Ustilago tritici*), stinking smut (*Tilletia caries, Tilletia controversa*), eyespot (*Pseudocercosporella herpotrichoides*), leaf blotch (*Septoria tritici*), glume blotch (*Stagonospora nodorum*), tan spot (*Pyrenophora tritici-repentis*), rhizoctonia seeding blight (*Rhizoctonia solani*), take-all disease (*Gaeumannomyces graminis*), and blast (*Pyricularia graminis-tritici*);

Barley Diseases:
  powdery mildew (*Blumeria graminis*), fusarium head blight (*Fusarium graminearum, Fusarium avenaceum, Fusarium culmorum, Microdochium nivale*), stripe rust (*Puccinia striiformis*), stem rust (*Puccinia graminis*), dwarf leaf rust (*Puccinia hordei*), loose smut (*Ustilago nuda*), scald (*Rhynchosporium secalis*), net blotch (*Pyrenophora teres*), spot blotch (*Cochliobolus sativus*), stripe (*Pyrenophora graminea*), Ramularia disease (*Ramularia collo-cygni*), and rhizoctonia seeding blight (*Rhizoctonia solani*);

Corn Diseases:
  rust (*Puccinia sorghi*), southern rust (*Puccinia polysora*), northern leaf blight (*Setosphaeria turcica*), tropical rust (*Physopella zeae*), southern leaf blight (*Cochliobolus heterostrophus*), anthracnose (*Colletotrichum graminicola*), gray leaf spot (*Cercospora zeae-maydis*), eyespot (*Kabatiella zeae*), phaeosphaeria leaf spot (*Phaeosphaeria maydis*), Diplodia rot (*Stenocarpella maydis, Stenocarpella macrospora*), stalk rot (*Fusarium graminearum, Fusarium verticilioides, Colletotrichum graminicola*), smut (*Ustilago maydis*), and Physoderma brown spot and Physoderma stalk rot (*Physoderma maydis*);

Cotton Diseases:
  anthracnose (*Colletotrichum gossypii*), grey mildew (*Ramularia areola*), alternaria leaf spot (*Alternaria macrospora, Alternaria gossypii*), and Black root rot (*Thielaviopsis basicola*);

Coffee Diseases:
  rust (*Hemileia vastatrix*), and leaf spot (*Cercospora coffeicola*);

Rape Seed Diseases:
  sclerotinia rot (*Sclerotinia sclerotiorum*), gray leaf spot (*Alternaria brassicae*), root rot (*Phoma lingam*), and light leaf spot (*Pyrenopeziza brassicae*);

Sugar Cane Diseases:
  rust (*Puccinia melanocephela, Puccinia kuehnii*), and smut (*Ustilago scitaminea*);

Sunflower Diseases:
  rust (*Puccinia helianthi*), and downy mildew (*Plasmopara halstedii*);

Citrus Diseases:
  melanose (*Diaporthe citri*), scab (*Elsinoe fawcetti*), green mold (*Penicillium digitatum*), blue mold (*Penicillium italicum*), Phytophthora rot (*Phytophthora parasitica, Phytophthora citrophthora*), and aspergillus rot (*Aspergillus niger*);

Apple Diseases:
  blossom blight (*Monilinia mali*), valsa canker (*Valsa ceratosperma*), powdery mildew (*Podosphaera leucotricha*), alternaria leaf spot (*Alternaria alternata* apple pathotype), scab (*Venturia inaequalis*), bitter rot (*Glomerella cingulata, Colletotrichum acutatum*), blotch (*Diplocarpon mali*), ring rot (*Botryosphaeria berengeriana*), crown rot (*Phytophtora cactorum*), and rust (*Gymnosporangium juniperi-virginianae, Gymnosporangium yamadae*);

Pear Diseases:
  scab (*Venturia nashicola, Venturia pirina*), black spot (*Alternaria alternata* Japanese pear pathotype), and rust (*Gymnosporangium haraeanum*);

Peach Diseases:
  brown rot (*Monilinia fructicola*), scab (*Cladosporium carpophilum*), Phomopsis rot (*Phomopsis* sp.), and leaf curl (*Taphrina deformans*);

Grapes Diseases:
  anthracnose (*Elsinoe ampelina*), ripe rot (*Glomerella cingulata, Colletotrichum acutatum*), powdery mildew (*Uncinula necator*), rust (*Phakopsora ampelopsidis*), black rot (*Guignardia bidwellii*), and downy mildew (*Plasmopara viticola*);

Japanese Persimmon Diseases:
  anthracnose (*Gloeosporium kaki, Colletotrichum acutatum*), and leaf spot (*Cercospora kaki, Mycosphaerella nawae*);

Fig Diseases:
  rust (*Phakopsora nishidana*);

Diseases of Gourd Family:
  anthracnose (*Colletotrichum lagenarium*), powdery mildew (*Sphaerotheca fuliginea*), gummy stem blight (*Didymella bryoniae*), Corynespora leaf spot (*Corynespora cassiicola*), fusarium wilt (*Fusarium oxysporum*), downy mildew (*Pseudoperonospora cubensis*), phytophthora rot (*Phytophthora capsici*), and damping-off (*Pythium* sp.);

Tomato Diseases:
  early blight (*Alternaria solani*), leaf mold (*Cladosporium fulvum*), Cercospora leaf mold (*Pseudocercospora fuligena*), late blight (*Phytophthora infestans*), and powdery mildew (*Leveillula taurica*);

Eggplant Diseases:
  brown spot (*Phomopsis vexans*), and powdery mildew (*Erysiphe cichoracearum*);

Cruciferous Vegetables Diseases:
  alternaria leaf spot (*Alternaria japonica*), white spot (*Cercosporella brassicae*), clubroot (*Plasmodiophora brassicae*), downy mildew (*Peronospora parasitica*), and white rust (*Albugo candida*);

Welsh Onion Disease:
  rust (*Puccinia allii*);

Soybean Diseases:
  purple stain (*Cercospora kikuchii*), sphaceloma scab (*Elsinoe glycines*), pod and stem blight (*Diaporthe phaseolorum* var. *sojae*), rust (*Phakopsora pachyrhizi*), target spot (*Corynespora cassiicola*), anthracnose (*Colletotrichum* glycines, *Colletotrichum truncatum*), Rhizoctonia rot (*Rhizoctonia solani*), septoria brown spot (*Septoria glycines*), Cercospora leaf spot (*Cercospora sojina*), stem rot (*Sclerotinia sclerotiorum*), powdery mildew (*Microsphaera diffusa*), phytophthora stem and root rot (*Phytophthora sojae*), downy mildew (*Peronospora manshurica*), sudden death syndrome (*Fusarium virguliforme*), red crown rot (*Calonectria ilicicola*), and Diaporthe/Phomopsis complex (*Diaporthe longicolla*);

Kidney Bean Diseases:
  stem rot (*Sclerotinia sclerotiorum*), rust (*Uromyces appendiculatus*), angular leaf spot (*Phaeoisariopsis* griseola), anthracnose (*Colletotrichum lindemuthianum*), and Fusarium root-rot (*Fusarium solani*);

Peanut Diseases:
leaf spot (*Cercospora personata*), brown leaf spot (*Cercospora arachidicola*), southern blight (*Sclerotium rolfsii*), and Cylindrocladium black rot (*Calonectria ilicicola*);

Garden Pea Disease:
powdery mildew (*Erysiphe pisi*), and root rot (*Fusarium solani*);

Potato Diseases:
early blight (*Alternaria solani*), late blight (*Phytophthora infestans*), Pink rot (*Phytophthora erythroseptica*), powdery scab (*Spongospora subterranea* f. sp. *subterranea*), verticillium wilt (*Verticillium albo-atrum, Verticillium dahliae, Verticillium nigrescens*), dry rot (*Fusarium solani*), and potato wart (*Synchytrium endobioticum*);

Strawberry Disease:
powdery mildew (*Sphaerotheca humuli*);

Tea Diseases:
net blister blight (*Exobasidium reticulatum*), white scab (*Elsinoe leucospila*), gray blight (*Pestalotiopsis* sp.), and anthracnose (*Colletotrichum theae-sinensis*);

Tobacco Diseases:
brown spot (*Alternaria longipes*), anthracnose (*Colletotrichum tabacum*), blue mold (*Peronospora tabacina*), and black shank (*Phytophthora nicotianae*);

Sugar Beet Diseases:
cercospora leaf spot (*Cercospora beticola*), leaf blight (*Thanatephorus cucumeris*), root rot (*Thanatephorus cucumeris*), aphanomyces root rot (*Aphanomyces cochlioides*), and rust (*Uromyces betae*);

Rose Diseases:
black spot (*Diplocarpon rosae*), and powdery mildew (*Sphaerotheca pannosa*);

Chrysanthemum Diseases:
leaf blight (*Septoria chrysanthemi-indici*), and white rust (*Puccinia horiana*);

Onion Diseases:
botrytis leaf blight (*Botrytis cinerea, Botrytis byssoidea, Botrytis squamosa*), gray-mold neck rot (*Botrytis allii*), and small sclerotial neck rot (*Botrytis squamosa*);

Various Crops Diseases:
Botrytis rot (*Botrytis cinerea*), sclerotinia rot (*Sclerotinia sclerotiorum*), seedling blight (*Pythium aphanidermatum, Pythium irregulare, Pythium ultimum*);

Japanese Radish Disease:
alternaria leaf spot (*Alternaria brassicicola*);

Turfgrass Diseases:
dollar spot (*Sclerotinia homoeocarpa*), brown patch and large patch (*Rhizoctonia solani*), and pythium bligt (*Pythium aphanidermatum*);

Banana Disease:
Sigatoka disease (*Mycosphaerella fijiensis, Mycosphaerella musicola*);

Lentils Disease:
ascochyta blight (*Ascochyta lentis*);

Chickpea Disease:
ascochyta blight (*Ascochyta rabiei*);

Green Pepper Disease:
anthracnose (*Colletotrichum scovillei*);

Mango Disease:
anthracnose (*Colletotrichum acutatum*);

Fruit Trees Diseases:
white root rot (*Rosellinia necatrix*), and violet root rot (*Helicobasidium mompa*);

Postharvest Disease of Fruits (for Example, Apple and Pear):
Mucor rot diseases (*Mucor piriformis*);

Seed diseases or diseases in the early stages of the growth of various plants caused by *Aspergillus* spp., *Penicillium* spp., *Fusarium* spp., *Gibberella* spp., *Tricoderma* spp., *Thielaviopsis* spp., *Rhizopus* spp., *Mucor* spp., *Corticium* spp., *Phoma* spp., *Rhizoctonia* spp. or *Diplodia* spp., and the like;

Viral Diseases:
Lettuce big-vein disease transmitted by *Olpidium brassicae*, and viral diseases of several crops transmitted by Polymixa spp. (e.g. *Polymyxa betae* and *Polymyxa graminis*);

Diseases Caused by Bacteria:
bacterial seedling blight of rice (*Burkholderia plantarii*), bacterial spot of cucumber (*Pseudomonas syringae* pv. *Lachrymans*), bacterial wilt of eggplant (*Ralstonia solanacearum*), canker of citrus (*Xanthomonas citri*), bacterial soft rot of Chinese cabbage (*Erwinia carotovora*), scab of potato (*Streptomyces scabiei*), Goss's wilt of corn (*Clavibacter michiganensis*), Pierce's disease of grapes, olive and peach (*Xylella fastidiosa*), and crown gall of Rosaceae plants such as apple, peach, cherries (*Agrobacterium tumefaciens*).

The method for controlling plant diseases of the present invention is conducted by applying an effective amount of the Present crystal or the present composition to a plant or soil. Examples of the application method include foliar application, soil application, and seed application.

The Present crystal or the present composition is usually used by mixing it with inert carrier(s) such as solid carrier(s) and liquid carrier(s), and as needed, adding thereto surfactant(s), the other auxiliary agent(s) for formulation so as to be formulated into a solid formulation, and an aqueous suspension formulation. These formulations usually comprise 0.0001 to 99% by weight ratio of the Present crystal or the present composition.

Examples of the solid carrier include fine powders or granules of clays (for example, kaolin clay, diatomaceous earth, bentonite, or acid white clay), dry silica, wet silica, talcs, ceramics, the other inorganic minerals (for example, sericite, quartz, sulfur, active carbon, or calcium carbonate); as well as synthetic resins (for example, polyester resins such as polypropylene, polyacrylonitrile, polymethyl methacrylate or polyethylene terephthalate; nylon resins (for example, nylon-6, nylon-11, or nylon-66); polyamide resins; polyvinyl chloride, polyvinylidene chloride, vinyl chloride-propylene copolymers, and the others).

Examples of the liquid carriers include water; alcohols (for example, methanol, ethanol, isopropyl alcohol, butanol, hexanol, benzyl alcohol, ethylene glycol, propylene glycol, or phenoxy ethanol); ketones (for example, acetone, methyl ethyl ketone, or cyclohexanone); aromatic hydrocarbons (for example, toluene, xylene, ethyl benzene, dodecyl benzene, phenyl xylyl ethane, or methylnaphthalene); aliphatic hydrocarbons (for example, hexane, cyclohexane, kerosene, or light oil); esters (for example, ethyl acetate, butyl acetate, isopropyl myristate, ethyl oleate, diisopropyl adipate, diisobutyl adipate, or propylene glycol monomethyl ether acetate); nitriles (for example, acetonitrile, or isobutyronitrile); ethers (for example, diisopropyl ether, 1,4-dioxane, 1,2-dimethoxyethane, diethyleneglycol dimethyl ether, diethylene glycol monomethyl ether, propylene glycol monomethyl ether, dipropylene glycol monomethyl ether, or 3-methoxy-3-methyl-1-butanol); amides (for example, N,N-dimethylformamide, or N,N-dimethylacetamide); sulfoxides (for example, dimethyl sulfoxide); propylene carbonate; and vegetable oils (for example, soybean oil or cottonseed oil).

Examples of the nonionic surfactants include nonionic surfactants such as polyoxyethylenated alkyl ethers, polyoxyethylenated alkyl aryl ethers, and polyethylene glycol fatty acid esters; and anionic surfactants such as alkyl sulfonates, alkylbenzene sulfonates and alkyl sulfates. The specific examples of the surfactants include Nimbus (registered trademark), Assist (registered trademark), Aureo (registered trademark), Iharol (registered trademark), Silwet L-77 (registered trademark), BreakThru (registered trademark), Sundancell (registered trademark), Induce (registered trademark), Penetrator (registered trademark), AgriDex (registered trademark), Lutensol A8 (registered trademark), NP-7 (registered trademark), Triton (registered trademark), Nufilm (registered trademark), Emulgator NP7 (registered trademark), Emulad (registered trademark), TRITON X 45 (registered trademark), AGRAL 90 (registered trademark), AGROTIN (registered trademark), ARPON (registered trademark), EnSpray N (registered trademark), and BANOLE (registered trademark).

Examples of the other auxiliary agent(s) for formulation include a thickening agent, an antifoam agent, a preservative agent, an antifreezing agent, and the others.

Examples of the thickening agent include natural polysaccharides (such as xanthan gum, ramzan gum, locust bean gum, guar gum, carrageenan, welan gum, alginic acid, alginate, and tragacanth gum); mineral substance powders (such as aluminosilicate, magnesium aluminosilicate, smectite, bentonite, hecrite, synthetic hydrated silicic acid, and dry silica); and alumina sol.

When the present composition comprises a thickening agent, the total amounts thereof is usually within a range of 0.1 to 5% by weight as opposed to 100% by weight of the present composition.

Examples of the antifoam agent include silicone type antifoam agents (such as Antifoam C emulsion (Toray Dow Corning Corp. Product name), Antifoam CE (Toray Dow Corning Corp. Product name), Antifoam A Compound (Toray Dow Corning Corp. Product name), FS Antifoam 1266 (Toray Dow Corning Corp. Product name), KM-98 (Shin-Etsu Chemical Co., Ltd. Product name), KS-530 (Shin-Etsu Chemical Co., Ltd. Product name), KS-538 (Shin-Etsu Chemical Co., Ltd. Product name), BreakThrough AF5503 (Evonik Indusries AG Product name), Antifoam E-20 (Kao Corporation Product name), TSA730 (Momentive•Performance Materials•Japan LLC. Product name), TSA731 (Momentive•Performance Materials Japan LLC. Product name), TSA732 (Momentive•Performance Materials Japan LLC. Product name), YMA 6509 (Momentive•Performance Materials Japan LLC. Product name); fluoride type antifoam agents (such as Fluowet PL80 (Clariant International Ltd Product name)); and FoamStar W220 (Cognis Japan Ltd. Product name).

When the present composition comprises an antifoam agent, the total amounts thereof is usually within a range of 0.05 to 0.5% by weight as opposed to 100% by weight of the present composition.

Examples of the preservative agent include p-hydroxybenzoate ester, salicylic acid derivatives, 1,2-benzisothiazoline-3-one (such as Proxel GXL (Lonza K.K. Product name), and isothiazoline-3-one derivatives (such as BioHope L (K-I Chemical Industry Co. Ltd. Product name).

When the present composition comprises a preservative agent, the total amounts thereof is usually within a range of 0.01 to 3% by weight as opposed to 100% by weight of the present composition.

Examples of the antifreezing agent include Water-soluble glycols (such as ethylene glycol, and propylene glycol).

When the present composition comprises an antifreezing agent, the total amounts thereof is usually within a range of 1 to 20% by weight as opposed to 100% by weight of the present composition.

In the present invention, the plant encompasses whole plant and specific part(s) of the plant. Examples of the specific part of the plant include stem and leaf, flower, ear, fruit, tree stem, branch, crown, seed, vegetative reproductive organ, and seedling.

A vegetative reproduction organ means a part of plant such as root, stem, and leaf which has a growth capability even when said part is separated from the plant body and placed into soil. Examples of the vegetative reproduction organ include tuberous root, creeping root, bulb, corm or solid bulb, tuber, rhizome, stolon, rhizophore, cane cuttings, propagule, and vine cutting. Stolon is also referred to as "runner", and propagule is also referred to as "propagulum" and categorized into broad bud and bulbil. Vine cutting means a shoot (collective term of leaf and stem) of sweet potato, glutinous yam, or the like. Bulb, corm or solid bulb, tuber, rhizome, cane cuttings, rhizophore, and tuberous root are also collectively referred to as "bulb". For example, cultivation of potato starts with planting a tuber into soil, and the tuber to be used is generally referred to as "seed potato".

The application dose of the present crystal or the present composition may be varied depending on a climate condition, a formulation form, an application period, an application method, an application site, plant diseases to be controlled, plant to be applied, and the others. In the cases of foliar application or soil application, the application dose thereof is within a range of usually 1 to 500 g per 1,000 m$^2$. In the cases of seed application, the application dose of the present crystal or the present composition is within a range of 0.001 to 100 g per 1 Kg of seeds. In the cases where the present crystal or the present composition is formulated into an emulsifiable concentrate, a wettable powder, a flowable agent etc., these formulations are used by diluting them with water so as to make the active component's concentration 0.01 to 10,000 ppm, while the dust formulation or the granular formulation, etc., is usually applied as itself without diluting them.

Examples of the seed application (or seed treatments) include an application of the present crystal or the present composition to seeds, and specific examples thereof include spraying treatment in which a suspension of the present crystal or the present composition is sprayed onto seed surface or vegetative reproductive organ surface in the form of mist; smearing treatment in which the present crystal or the present composition is coated seeds surface or vegetative reproductive organ surface; a soaking treatment in which the seeds are soaked into the liquid comprising the present crystal or the present composition for a certain time; and a method for coating the seeds or the vegetative reproductive organ with a carrier containing the present crystal or the present composition (film coating treatment, pellet coating treatment). In particular, examples of the above-mentioned vegetative reproductive organ include "seed potato".

When the present composition is applied to seeds or vegetative reproductive organ, the present composition may be also applied to seeds or vegetative reproductive organ as a single formulation, or the present composition may be applied to seeds or vegetative reproductive organ as a divided plural of formulations by a plurality of times. Examples of the method in which the present composition is applied as a divided plural of formulations by a plurality of times include, for example, a method in which the formulations comprising as an active component the present crystal only are applied, and seeds or vegetative reproductive organ are air dried, followed by applying the formulations comprising the present ingredient; and a method in which the formulations comprising as an active component the present crystal and the present ingredients are applied, and seeds or vegetative reproductive organ are air dried, followed by applying the formulations comprising the present ingredients other than the already-applied present ingredients, are included.

As used herein, seeds or vegetative reproductive organs carrying the present crystal or the present composition means seeds or vegetative reproductive organs in the state where the present crystal or the present composition is adhered to a surface of the seeds or the vegetative reproductive organ. The above-described seeds or vegetative reproductive organs carrying the present crystal or the present composition may be adhered by any other materials that are different from the present crystal or the present composition before or after being adhered the present crystal or the present composition to the seeds or vegetative reproductive organs.

Also, when the present composition is adhered in a form of layer(s) to a surface of seeds or vegetative reproductive organ, the layer(s) is/are composed of one layer or a multiple layers. Also, when multiple layers are formed, each of the layer may be composed of a layer comprising one or more active ingredients, or a combination of a layer comprising one or more active ingredients and a layer not comprising an active ingredient.

Seeds or vegetative reproductive organs carrying the present compound or the Composition A can be obtained, for example, by applying the formulations comprising the present compound or the Composition A by the above-described application method to seeds or vegetative reproductive organs.

The present crystal or the present composition may be used as an agent for controlling plant diseases in agricultural lands such as fields, paddy fields, turfs, and orchards. Examples of the plants include the followings.

corn, rice, wheat, barley, rye, oat, sorghum, cotton, soybean, peanut, buckwheat, beet, rapeseed, sunflower, sugar cane, tobacco, solanaceous vegetables (for example, eggplant, tomato, pimento, pepper, or potato), cucurbitaceous vegetables (for example, cucumber, pumpkin, zucchini, water melon, or melon), cruciferous vegetables (for example, Japanese radish, white turnip, horseradish, kohlrabi, Chinese cabbage, cabbage, leaf mustard, broccoli, or cauliflower), asteraceous vegetables (for example, burdock, crown daisy, artichoke, or lettuce), liliaceous vegetables (for example, green onion, onion, garlic, or asparagus), ammiaceous vegetables (for example, carrot, parsley, celery, or parsnip), chenopodiaceous vegetables (for example, spinach, or Swiss chard), lamiaceous vegetables (for example, *Perilla frutescens*, mint, or basil), strawberry, sweet potato, *Dioscorea japonica, colocasia*, pomaceous fruits (for example, apple, pear, Japanese pear, Chinese quince, or quince), stone fleshy fruits (for example, peach, plum, nectarine, Prunus mume, cherry fruit, apricot, or prune), citrus fruits (for example, Citrus unshiu, orange, lemon, lime, or grapefruit), nuts (for example, chestnut, walnuts, hazelnuts, almond, pistachio, cashew nuts, or macadamia nuts), berry fruits (for example, blueberry, cranberry, blackberry or raspberry), grape, kaki persimmon, olive, Japanese plum, banana, coffee, date palm, coconuts, tea, mulberry, ornamental foliage plants, woodland plants, lawns, pastures.

The above-mentioned plants include also genetically modified crops.

EXAMPLES

Hereinafter, the present invention is explained in more detail by indicating Preparation examples, Reference preparation examples, Formulation examples, and Test examples, however, the present invention should not be limited to these examples.

Here in the working examples, "%" and "part" represents "weight %" and "weight part" unless otherwise indicated.

Also for the prepared present crystal form, various physical properties were measured using a device (with measurement conditions) as shown below.

Powder XRD
    Powder x-ray diffractometer: Smartlab (manufactured by Rigaku Corporation)
    X-ray output: Cu-Kα, 45 kV, 200 mA
    Sampling range: 0.02°
    Scan range: 2° to 50°
    Measured temperature: Room temperature Single-Crystal XRD
(Ra1 Type Crystal Form)
    Device: R-AXIS RAPID (manufactured by Rigaku Corporation)
    X-ray source: Mo-Kα
    Measured temperature:Room temperature
    Solve: SHELXT
    Refinement: SHELXL
(Ra2 Type Crystal Form)
    Device: R-AXIS RAPID (manufactured by Rigaku Corporation)
    X-ray source: Mo-Kα
    Measured temperature:Room temperature
    Solve: SIR2014
    Refinement: SHELXL
(Ra3 Type Crystal Form)
    Device: XtaLAB Synergy (manufactured by Rigaku Corporation)
    X-ray source: Cu-Kα
    Measured temperature: 100 K
    Solve: SHELXT
    Refinement: SHELXL DSC
    Device: DSC Q2000 (manufactured by TA instrument)
    Rate of temperature increase: 2° C./min
    Sample amount: 0.5 to 5 mg
    Measured atmosphere: Nitrogen Fourier Transform Infrared Spectroscopy (FT-IR)
    Device: Nicolet iS50 (manufactured by Thermo Fisher Scientific Inc.)
    Measurement method: Diamond ATR method Microscopic Raman Spectroscopy
    Device: NRS-5100 (manufactured by JASCO Corporation)
    Laser wavelength: 532 nm Optical Microscope
  Optical microscope: Leica Z16 APO (manufactured by Leica Microsystems)
  Camera: Leica MC170 HD (manufactured by Leica Microsystems)
  Magnification: 115 magnifications A preparation example of the present crystal is described.

Preparation Example 1

Preparation of Ra2 Type Crystal Form

The compound A 30 mg was dissolved in methanol at 60° C. so as to adjust it to be 375 mg/mL. After the resulting solution was cooled to room temperature, the mixture was irradiated with laser under the below-mentioned condition, and it was then allowed to stand at 20° C. to obtain the Ra2 type crystal form.

The laser irradiation condition was described below.
<Femtosecond Laser>
  Wavelength: 800 nm
  Pulse width: 181 fs
  Number of pulse: 125 pulse/10 seconds Preparation Example 2

Preparation of Ra1 Type Crystal Form

The Ra2 type crystal form 200 mg which was obtained in the preparation example 1 was weighted in a 20 mL volume sample bottle, and it was heated at 130° C. for 2 hours to obtain the Ra1 type crystal form.

Preparation Example 3

Preparation of Ra3 Type Crystal Form

To the Ra1 type crystal form 100 mg obtained in the preparation example 2, diisopropyl ether 1 mL was added, and the resulting suspension was heated to 60° C., and stirred at 1,000 rpm for 2 days, and the solvents were removed to obtain the Ra3 type crystal form.

Reference Preparation Example 1

Preparation of Ra4 Type Crystal Form

With respect to the preparation of the Ra4 type crystal form, the compound A was dissolved in toluene and then was recrystallized according to the process described in WO 92/12970 (Patent Literature 1) to prepare the Ra4 type crystal form.

The physical properties of the present crystal(s) are indicated below.
Ra1 Type Crystal Form
  IR characteristic peak: 2933.0, 1648.4, 1632.0, 1606.6, 1554.6, 1338.8, 1082.9, and 1036.5 $cm^{-1}$.
  Raman characteristic peak: peaks around 2946, 2927, 2858, 1649, 1631, and 1397 $cm^{-1}$.
XRD Characteristic Peak:
  With respect to the characteristic diffraction peak(s) in the powder x-ray diffraction pattern as shown in FIG. 1, the diffraction peak value(s) as a diffraction angle (2θ±0.2°) is indicated in Table 1, which are not limited thereto.

Table 1

TABLE 1

| Peak No. | 2θ(°) | d value [Å] | Relative intensity [%] |
|---|---|---|---|
| 1 | 7.1 ± 0.2 | 12.4 | 24.2 |
| 2 | 8.6 ± 0.2 | 10.3 | 100 |
| 3 | 8.9 ± 0.2 | 9.9 | 68.4 |
| 4 | 9.1 ± 0.2 | 9.7 | 83.1 |
| 5 | 10.1 ± 0.2 | 8.7 | 10.9 |
| 6 | 13.3 ± 0.2 | 6.7 | 18.4 |
| 7 | 14.0 ± 0.2 | 6.3 | 19.0 |
| 8 | 14.3 ± 0.2 | 6.2 | 30.0 |
| 9 | 14.8 ± 0.2 | 6.0 | 24.0 |
| 10 | 16.0 ± 0.2 | 5.5 | 90.9 |
| 11 | 16.4 ± 0.2 | 5.4 | 59.2 |
| 17 | 20.3 ± 0.2 | 4.4 | 34.9 |
| 18 | 20.6 ± 0.2 | 4.3 | 20.4 |

Typical examples of the diffraction peaks include 7.1±0.2, 8.6±0.2, 8.9±0.2, 9.1±0.2, 13.3±0.2, 14.0±0.2, 14.3±0.2, 14.8±0.2, 16.0±0.2, and 16.4±0.2 as indicated in Table 1.

Figure 2:
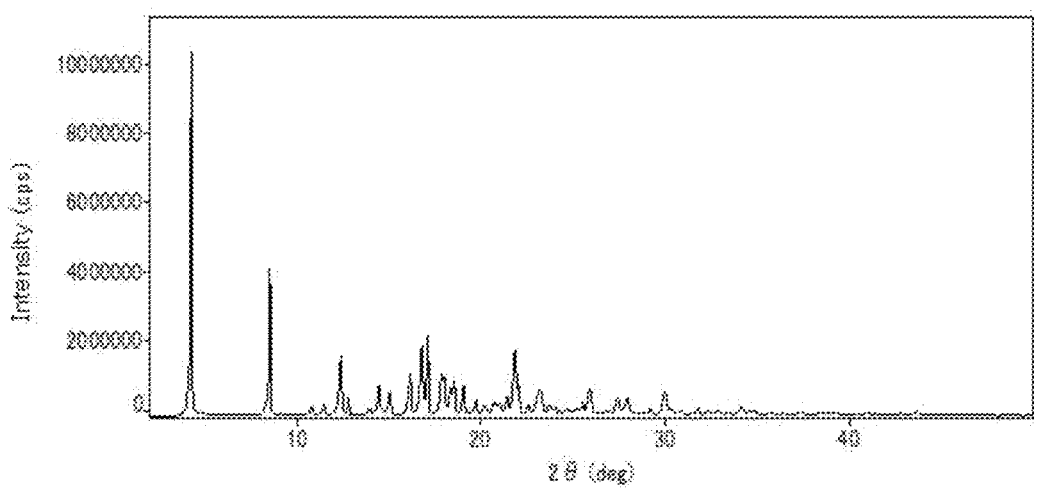
FIG. 2 is a figure showing powder x-ray diffraction patterns of Ra2 type crystal form. The vertical axis represents diffraction intensity (unit: cps) and the horizontal axis represents diffraction angle (2θ) (unit: °).

Ra2 Type Crystal Form
  IR characteristic peak: 3292.4, 2957.1, 2927.5, 1659.1, 1642.0, 1544.1, 1133.5, and 1123.2 $cm^{-1}$.
  Raman characteristic peak: peaks around 3118, 2924, 2876, 1658, and 1641 $cm^{-1}$.
XRD Characteristic Peak:
  With respect to the characteristic diffraction peak(s) in the powder x-ray diffraction pattern as shown in FIG. 2, the diffraction peak value(s) as a diffraction angle (2θ±0.2°) is indicated in Table 2, which are not limited thereto.

Table 2

TABLE 2

| Peak No. | 2θ(°) | d value [Å] | Relative intensity [%] |
|---|---|---|---|
| 1 | 4.3 ± 0.2 | 20.8 | 100 |
| 2 | 8.5 ± 0.2 | 10.4 | 41.9 |
| 3 | 10.8 ± 0.2 | 8.2 | 2.8 |
| 4 | 11.4 ± 0.2 | 7.7 | 4.2 |
| 5 | 12.4 ± 0.2 | 7.1 | 27.9 |
| 6 | 12.8 ± 0.2 | 6.9 | 4.3 |
| 7 | 15.1 ± 0.2 | 5.9 | 10.2 |
| 8 | 16.1 ± 0.2 | 5.5 | 17.3 |
| 9 | 16.8 ± 0.2 | 5.3 | 35.9 |
| 10 | 19.1 ± 0.2 | 4.7 | 12.8 |

Typical examples of the diffraction peaks include 4.3±0.2, 8.5±0.2, 10.8±0.2, 11.4±0.2, 12.4±0.2, 12.8±0.2, 15.1±0.2, 16.1±0.2, 16.8±0.2, and 19.1±0.2 as indicated in Table 2.

Figure 3:
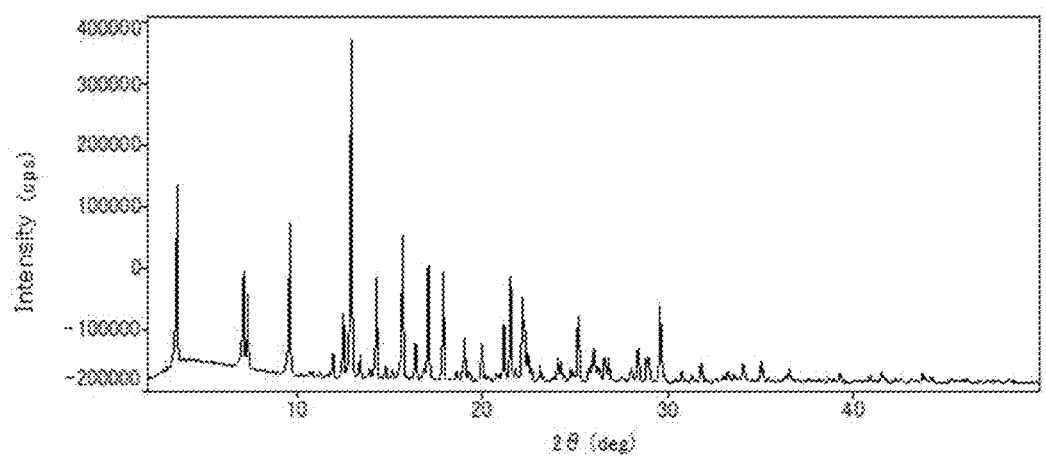
FIG. 3 is a figure showing powder x-ray diffraction patterns of Ra3 type crystal form. The vertical axis represents diffraction intensity (unit: cps) and the horizontal axis represents diffraction angle (2θ) (unit: °).

Ra3 Type Crystal Form
  IR characteristic peak: 3301.7, 2959.1, 2858.1, 1654.4, 1644.3, 1545.6, 1518.3, 1133.9, 1123.3, and 1032.8 $cm^{-1}$.
  Raman characteristic peak: peaks around 3046, 2928, 1652, 1588, and 1545 $cm^{-1}$.
XRD Characteristic Peak:
  With respect to the characteristic diffraction peak(s) in the powder x-ray diffraction pattern as shown in FIG. 3, the diffraction peak value(s) as a diffraction angle (2θ±0.2°) is indicated in Table 3, which are not limited thereto.

Table 3

TABLE 3

| Peak No. | 2θ(°) | d value [Å] | Relative intensity [%] |
|---|---|---|---|
| 1 | 3.6 ± 0.2 | 24.7 | 56.6 |
| 2 | 7.1 ± 0.2 | 12.4 | 28.1 |
| 3 | 7.4 ± 0.2 | 12.0 | 21.5 |
| 4 | 9.6 ± 0.2 | 9.2 | 46.6 |
| 5 | 11.9 ± 0.2 | 7.4 | 7.1 |
| 6 | 12.5 ± 0.2 | 7.1 | 14.2 |
| 7 | 12.9 ± 0.2 | 6.8 | 100 |
| 8 | 14.3 ± 0.2 | 6.2 | 28.4 |
| 9 | 15.7 ± 0.2 | 5.6 | 47.0 |
| 10 | 17.9 ± 0.2 | 5.0 | 29.7 |

Typical examples of the diffraction peaks include 3.6±0.2, 7.1±0.2, 7.4±0.2, 9.6±0.2, 11.9±0.2, 12.5±0.2, 12.9±0.2, 14.3±0.2, 15.7±0.2, and 17.9±0.2 as indicated in Table 3.

In order to compare with the Ra1 type crystal form, the Ra2 type crystal form, and the Ra3 type crystal form of the present invention, each kind of spectral value of the Ra4 type crystal form is shown below.

Ra4 Type Crystal Form

IR characteristic peak: 2953.8, 1635.5, 1608.7, 1553.2, 1138.7, 1066.8, 1034.2, and 1012.3 $cm^{-1}$.

Raman characteristic peak: peaks around 2928, 2859, 1491, 1398, and 1311 $cm^{-1}$.

XRD Characteristic Peak

Figure 4:
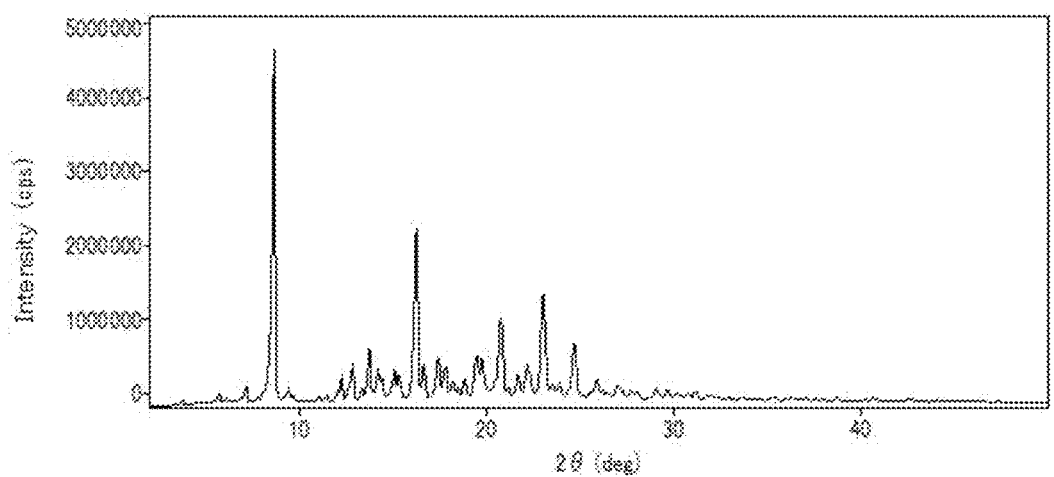
FIG. 4 is a figure showing powder x-ray diffraction patterns of Ra4 type crystal form. The vertical axis represents diffraction intensity (unit: cps) and the horizontal axis represents diffraction angle (2θ) (unit: °).
Figure 5:
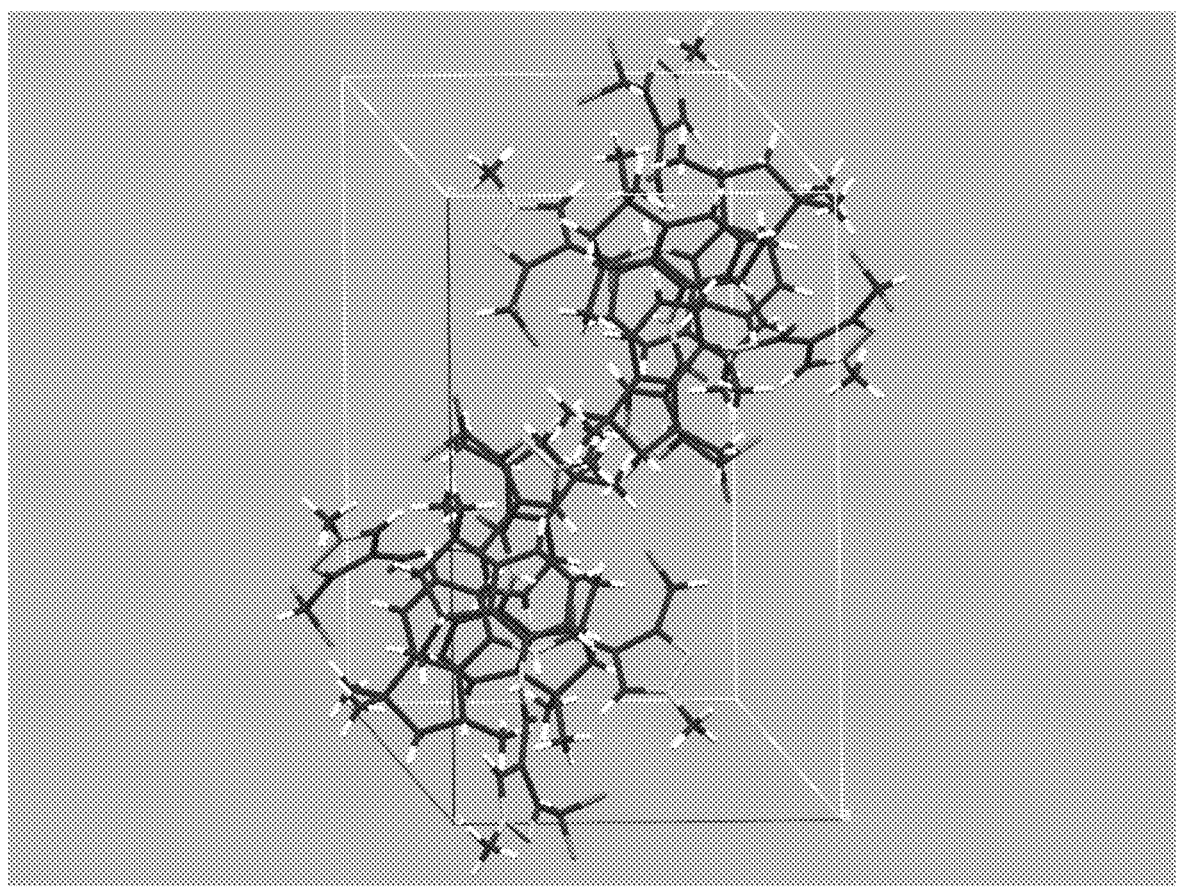
FIG. 5 is a figure showing a molecular packing in a crystal lattice of Ra1 type crystal form.
Figure 6:
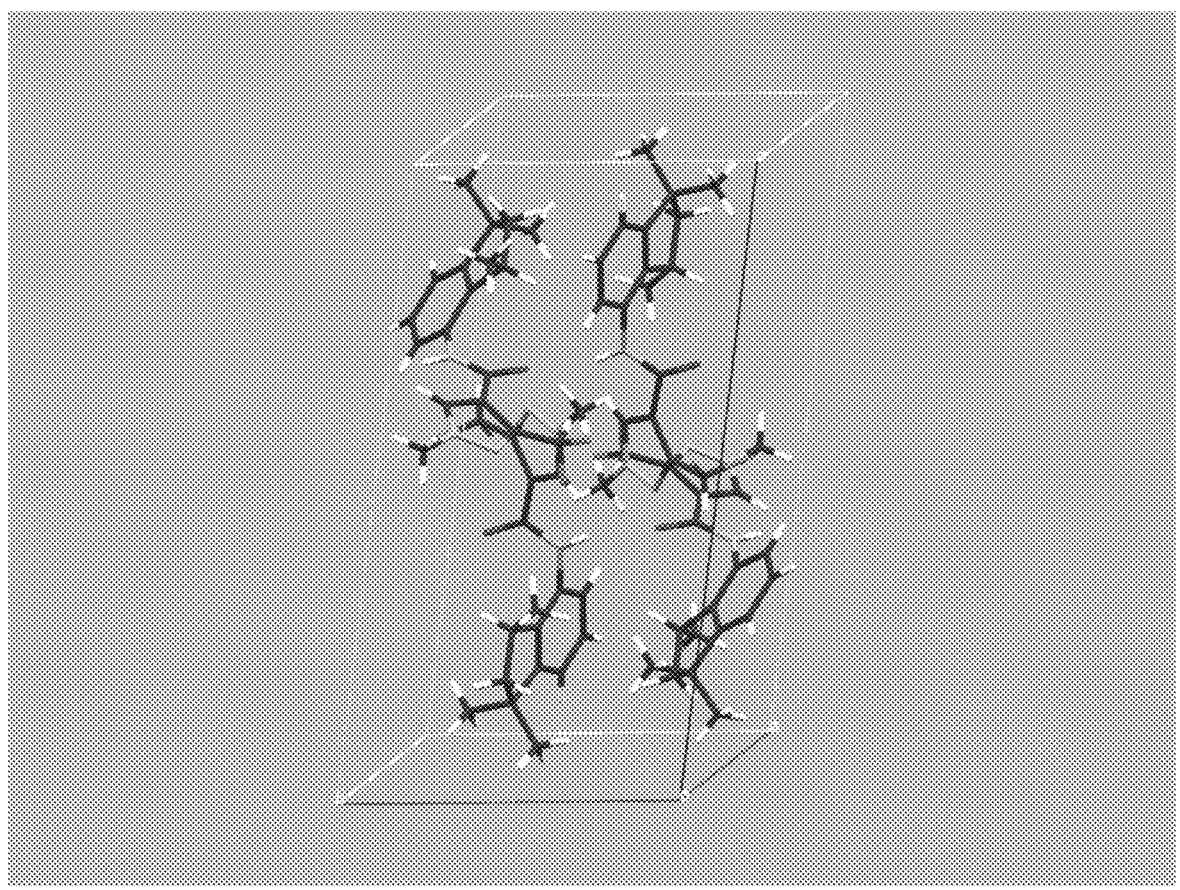
FIG. 6 is a figure showing a molecular packing in a crystal lattice of Ra2 type crystal form.
Figure 7:
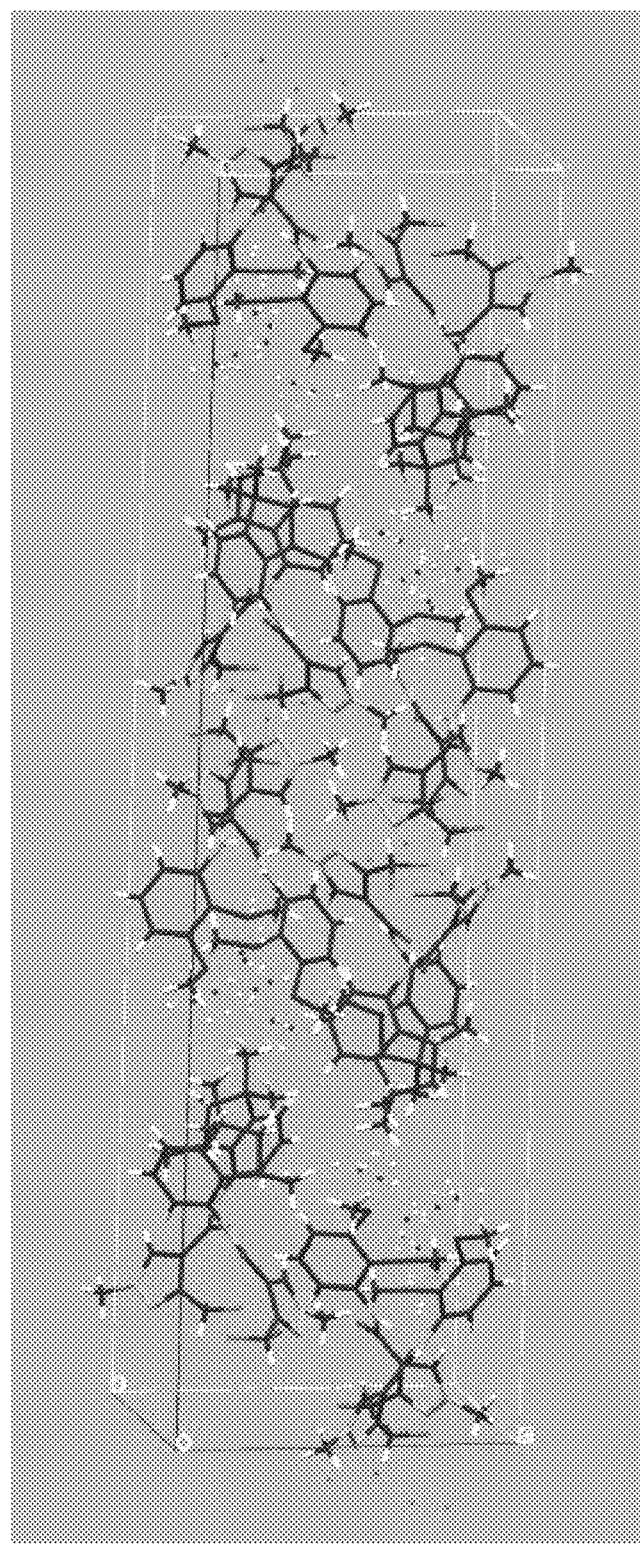
FIG. 7 is a figure showing a molecular packing in a crystal lattice of Ra3 type crystal form.
Figure 8:
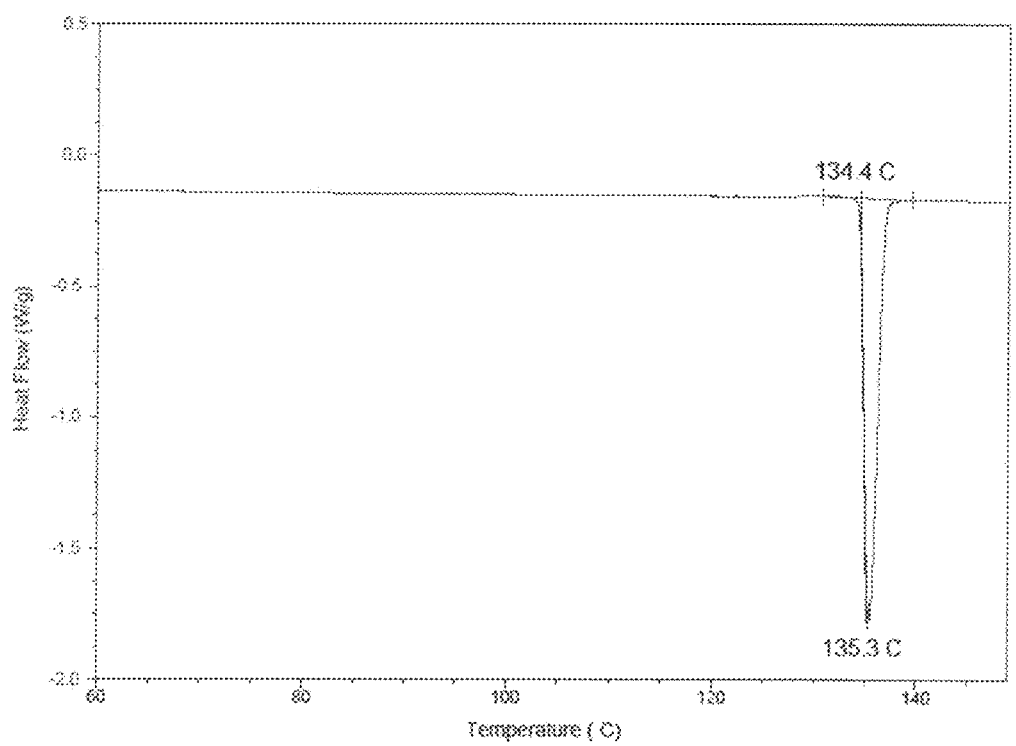
FIG. 8 is a figure showing a differential scanning calorimetry (DSC) curve of Ra1 type crystal form. The vertical axis represents heat flow (unit: W/g) and the horizontal axis represents temperature (unit: ° C.).
Figure 9:
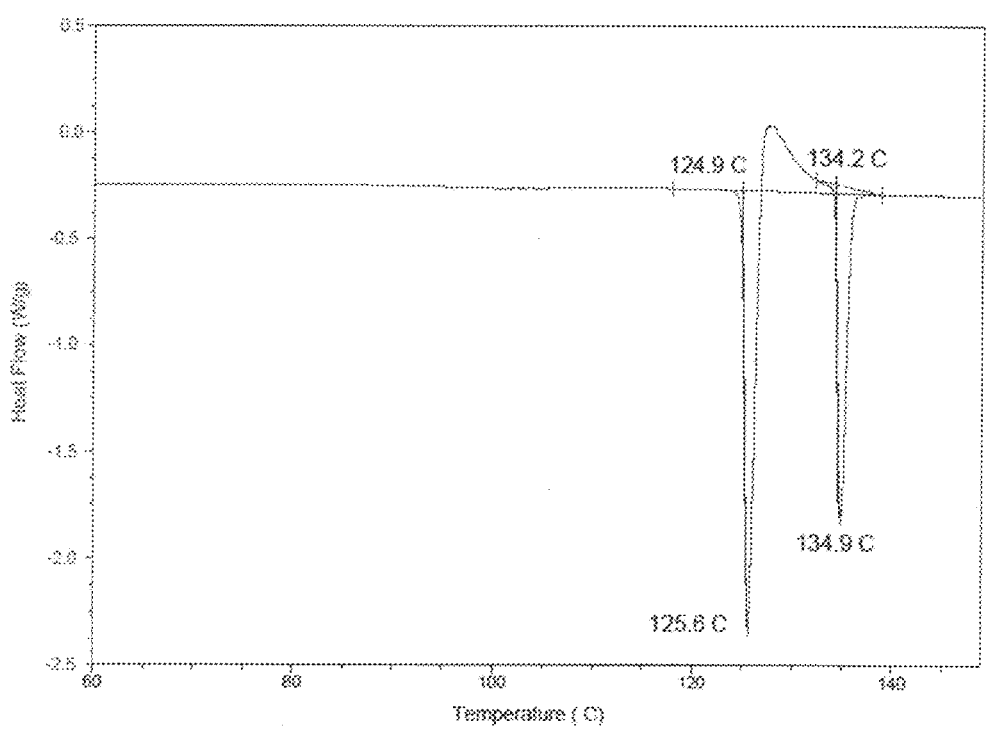
FIG. 9 is a figure showing a differential scanning calorimetry (DSC) curve of Ra2 type crystal form.
Figure 10:
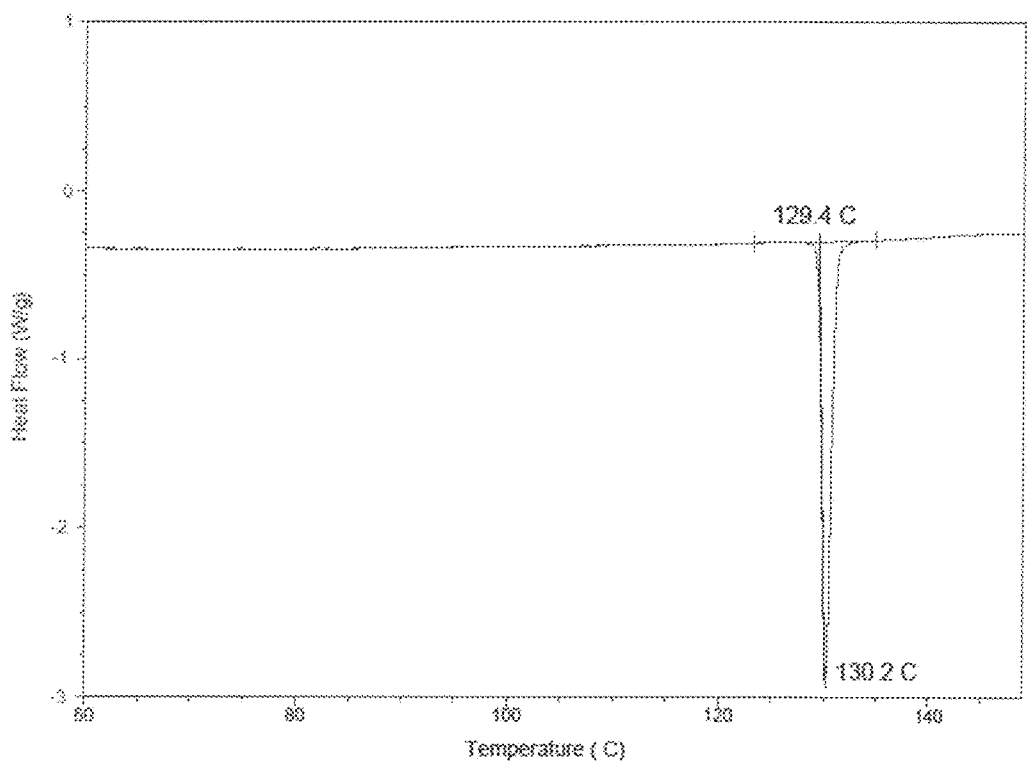
FIG. 10 is a figure showing a differential scanning calorimetry (DSC) curve of Ra3 type crystal form.
Figure 11:
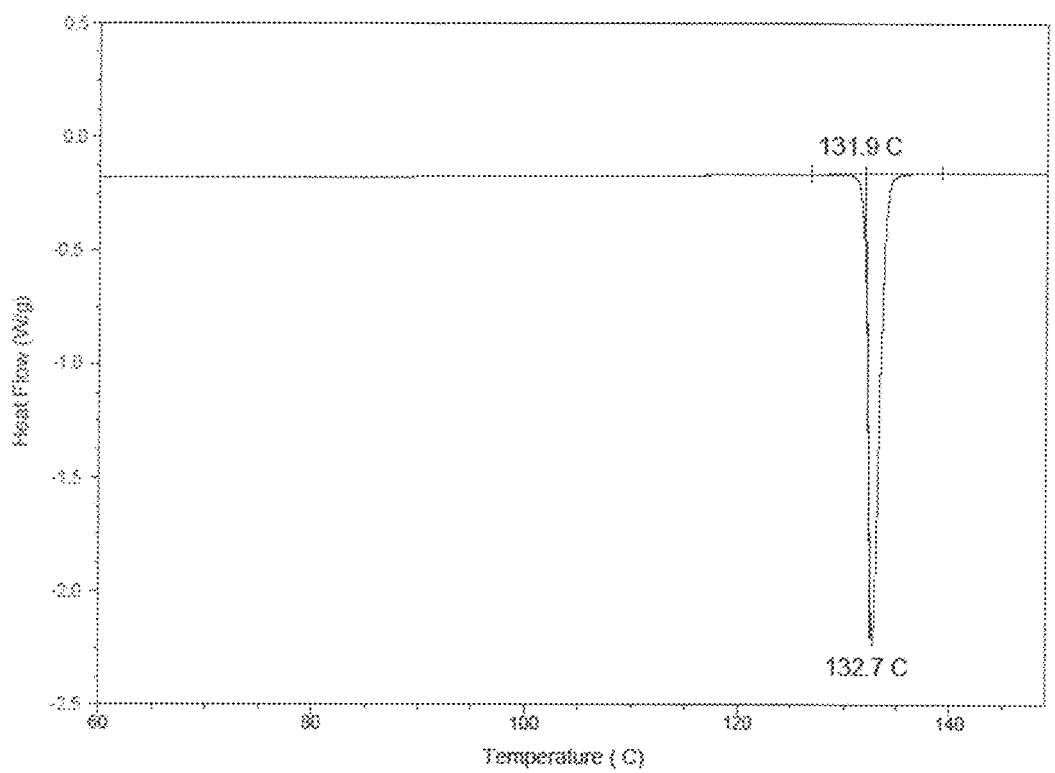
FIG. 11 is a figure showing a differential scanning calorimetry (DSC) curve of Ra4 type crystal form.
Figure 12:
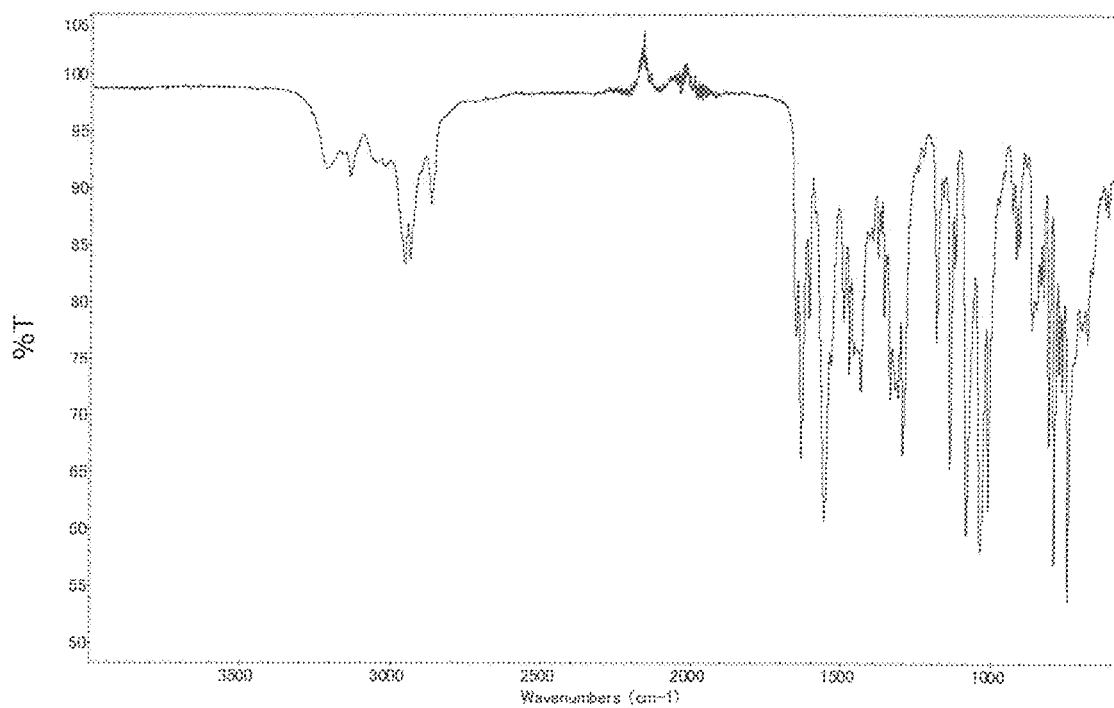
FIG. 12 is a figure showing a spectral diagram of infrared spectrum of Ra1 type crystal form. The vertical axis represents a transmittance and the horizontal axis represents an irradiated infrared wavenumber.
Figure 13:
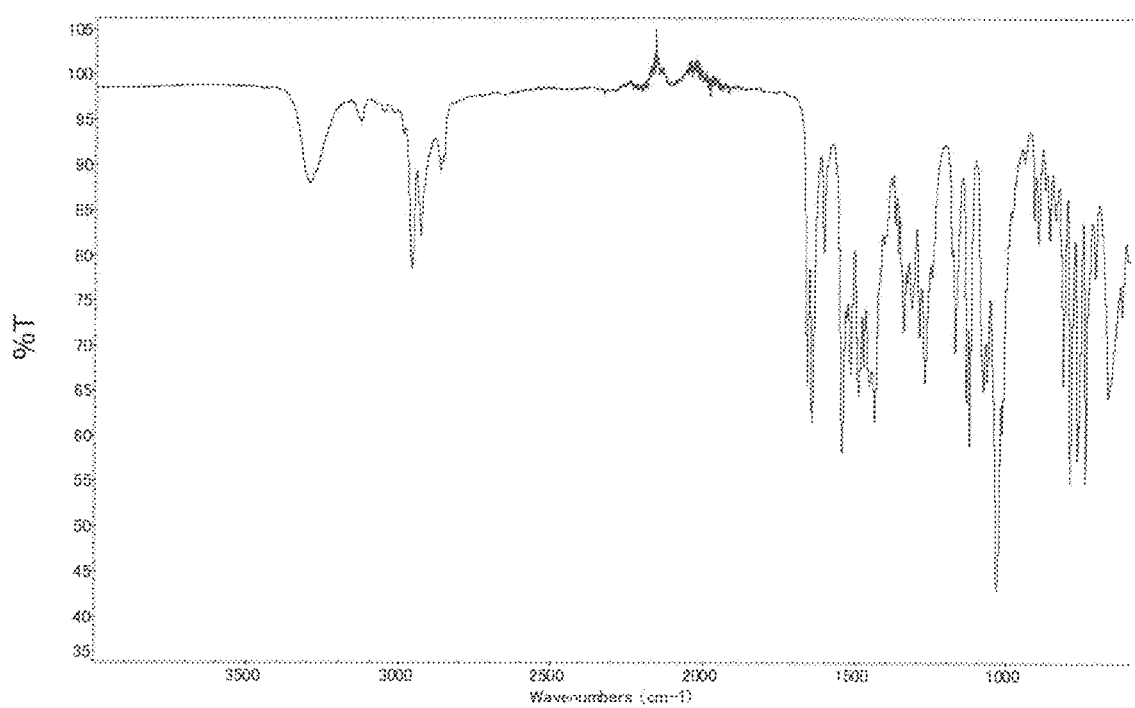
FIG. 13 is a figure showing a spectral diagram of infrared spectrum of Ra2 type crystal form. The vertical axis represents a transmittance and the horizontal axis represents an irradiated infrared wavenumber.
Figure 14:
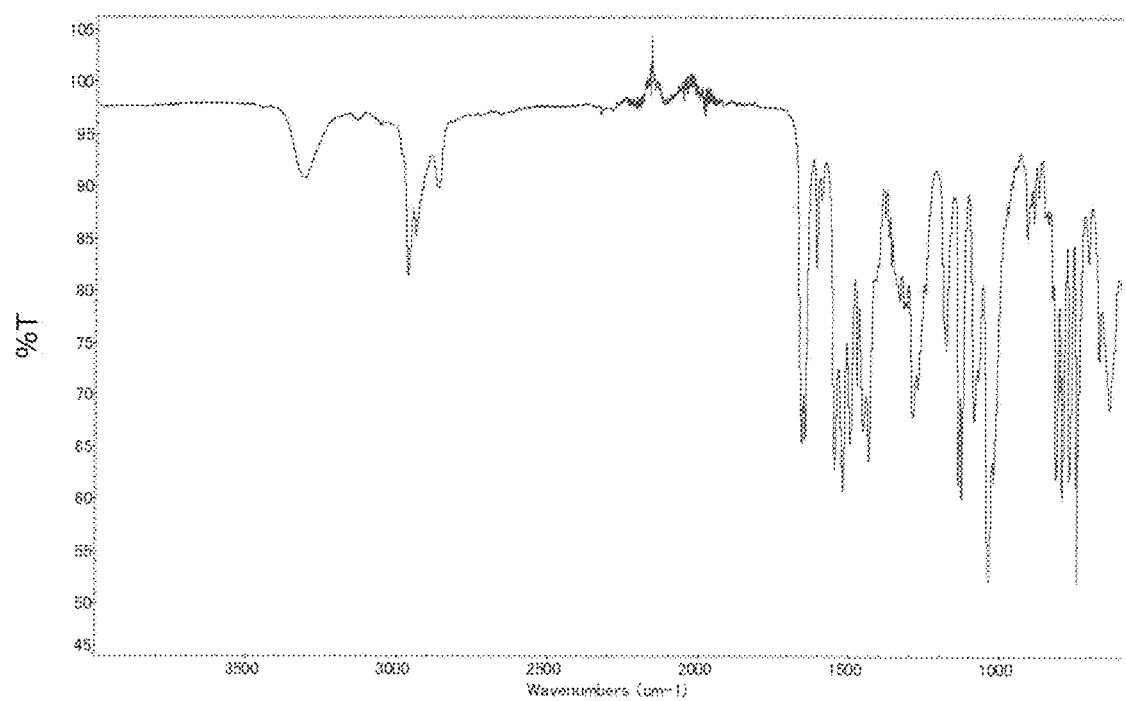
FIG. 14 is a figure showing a spectral diagram of infrared spectrum of Ra3 type crystal form. The vertical axis represents a transmittance and the horizontal axis represents an irradiated infrared wavenumber.
Figure 15:
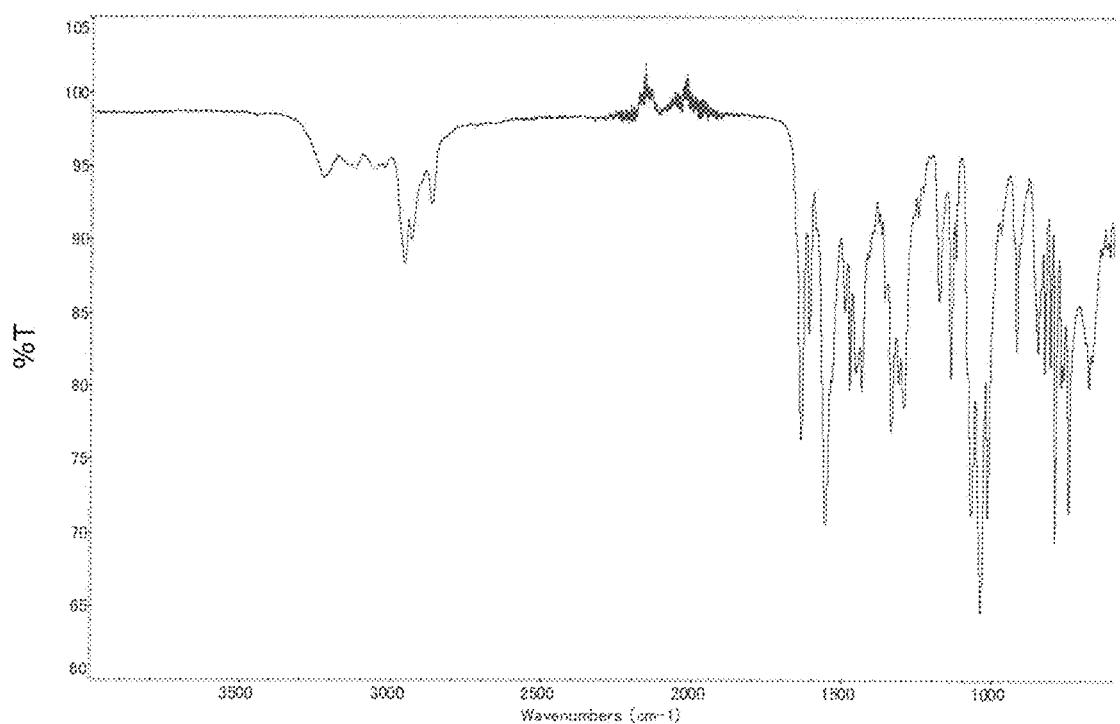
FIG. 15 is a figure showing a spectral diagram of infrared spectrum of Ra4 type crystal form. The vertical axis represents a transmittance and the horizontal axis represents an irradiated infrared wavenumber.
Figure 16:
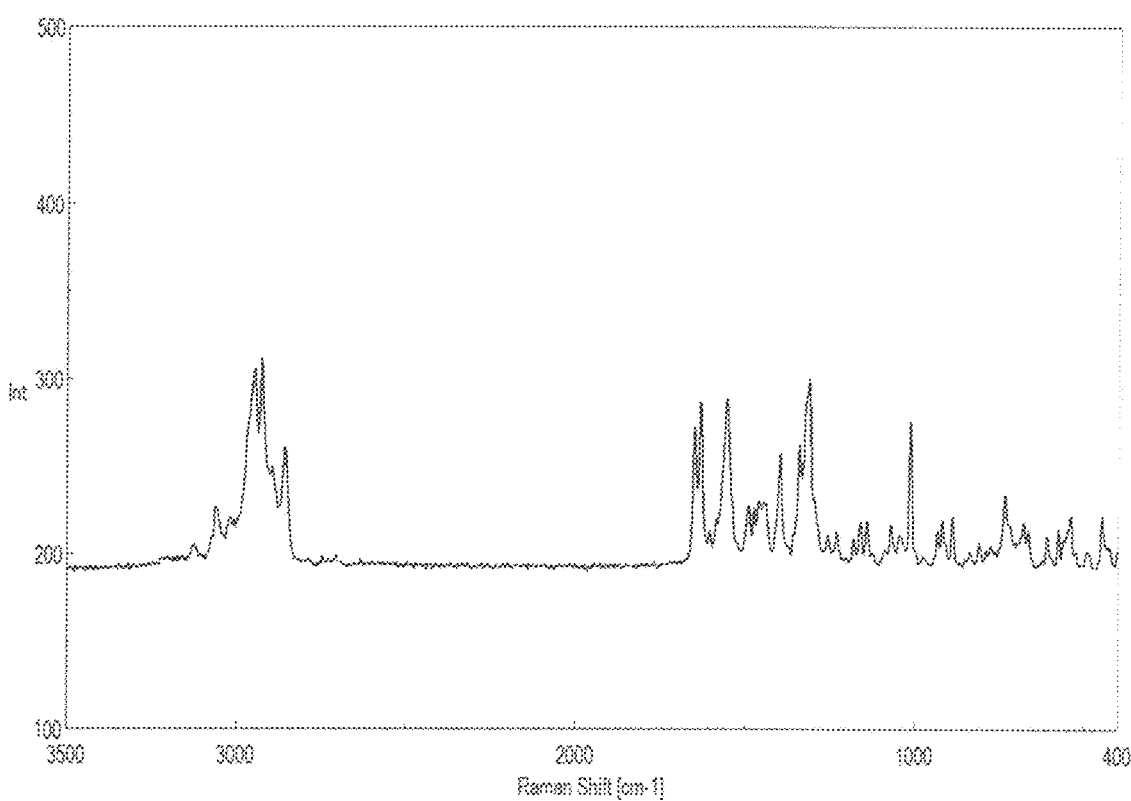
FIG. 16 is a figure showing a spectral diagram of Raman spectrum of Ra1 type crystal form. The vertical axis represents an intensity and the horizontal axis represents a Raman shift number.
Figure 17:
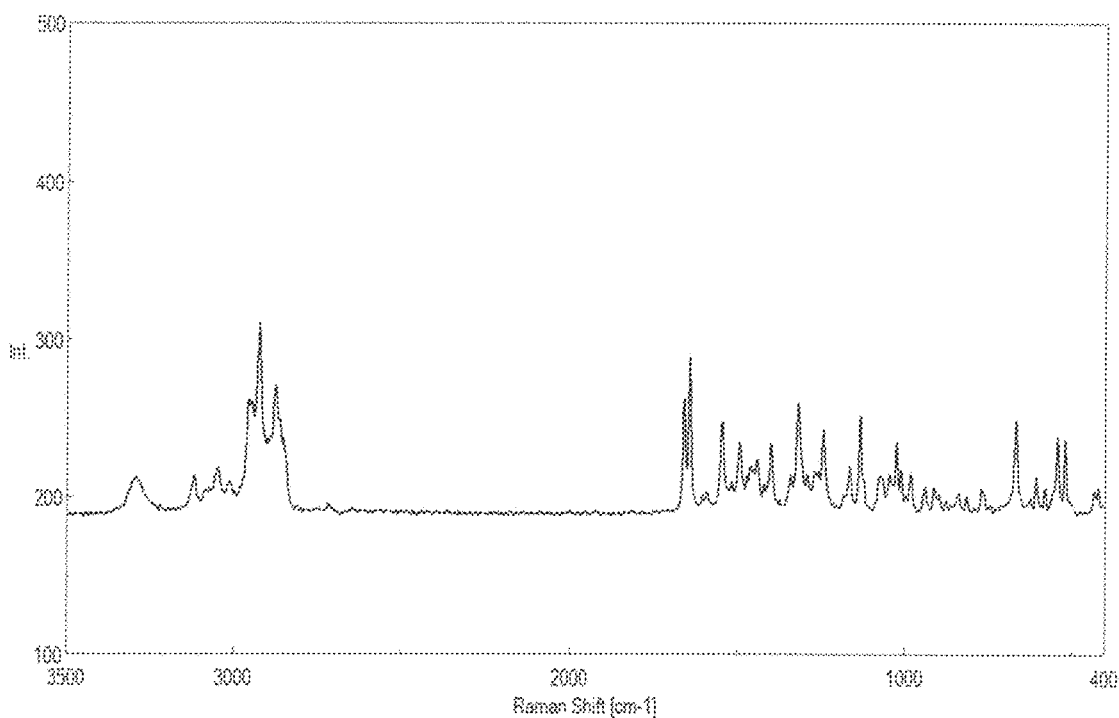
FIG. 17 is a figure showing a spectral diagram of Raman spectrum of Ra2 type crystal form. The vertical axis represents an intensity and the horizontal axis represents a Raman shift number.
Figure 18:
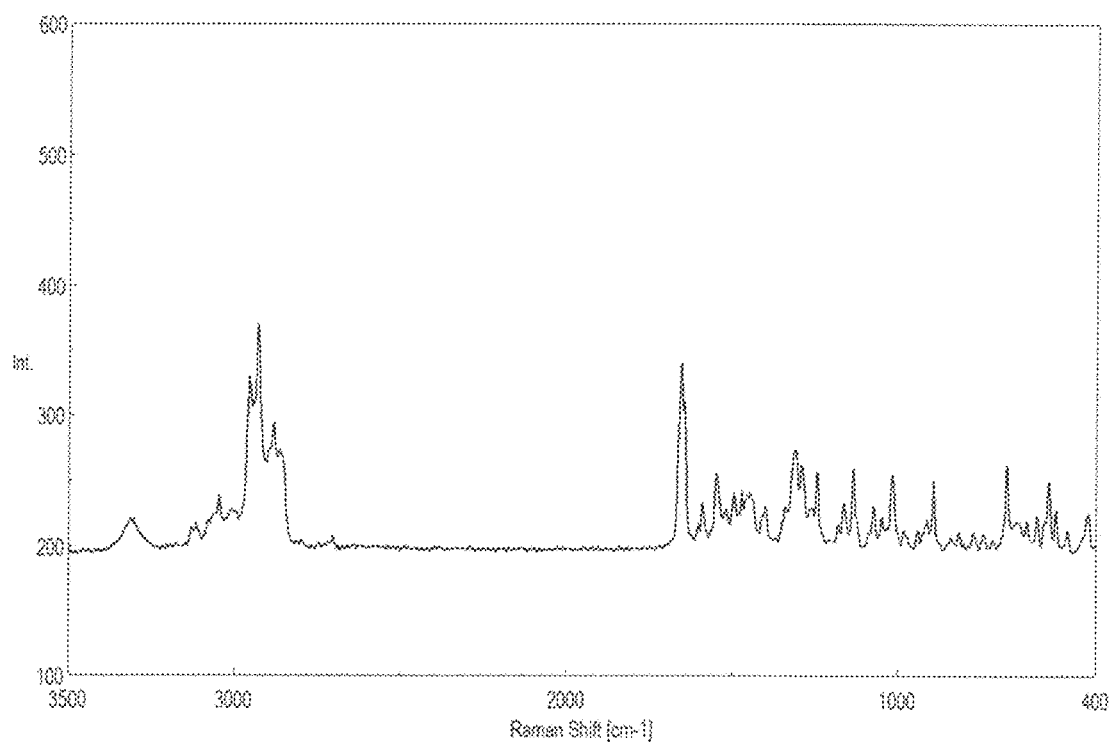
FIG. 18 is a figure showing a spectral diagram of Raman spectrum of Ra3 type crystal form. The vertical axis represents an intensity and the horizontal axis represents a Raman shift number.
Figure 19:
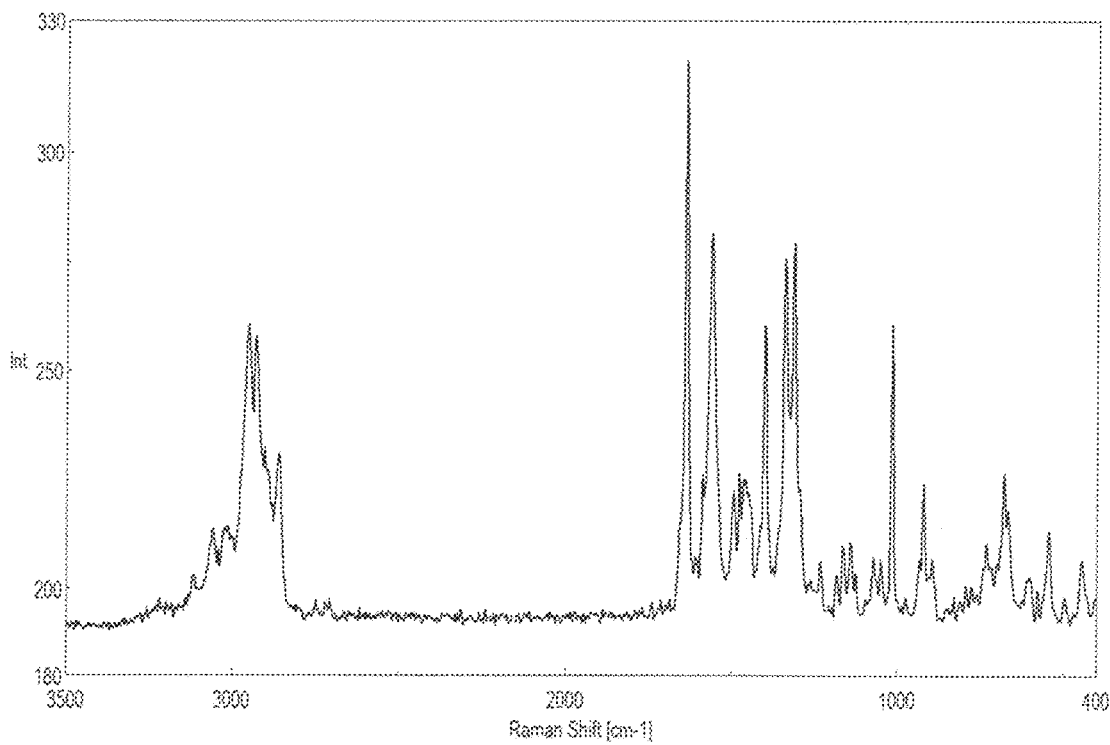
FIG. 19 is a figure showing a spectral diagram of Raman spectrum of Ra4 type crystal form. The vertical axis represents an intensity and the horizontal axis represents a Raman shift number.
Figure 20:
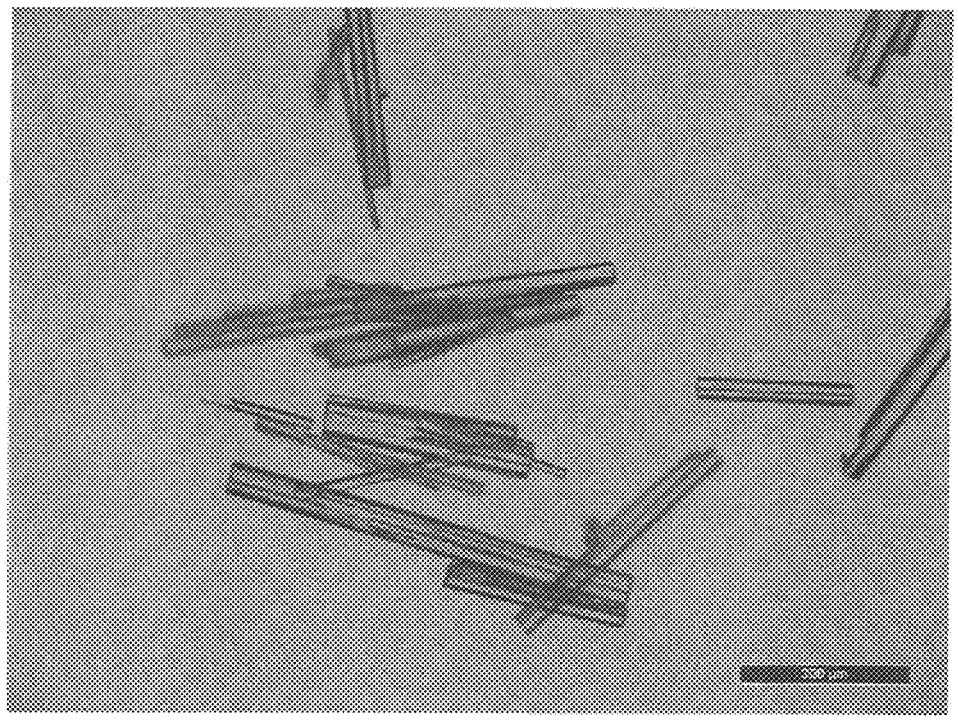
FIG. 20 is a figure showing a photograph of optical microscope of Ra1 type crystal form.
Figure 21:
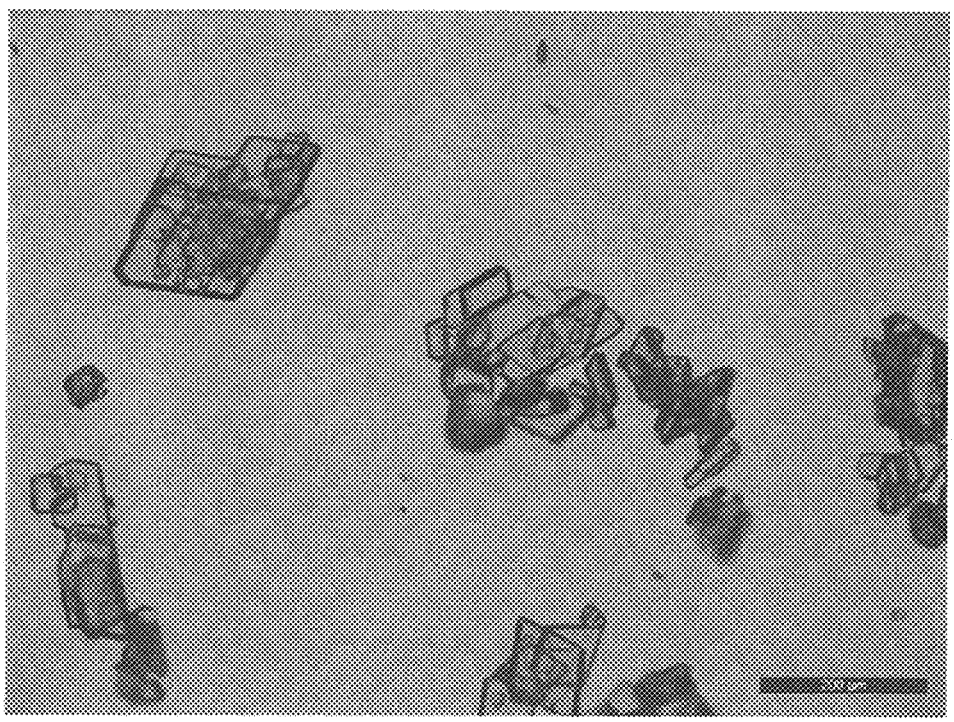
FIG. 21 is a figure showing a photograph of optical microscope of Ra2 type crystal form.
Figure 22:
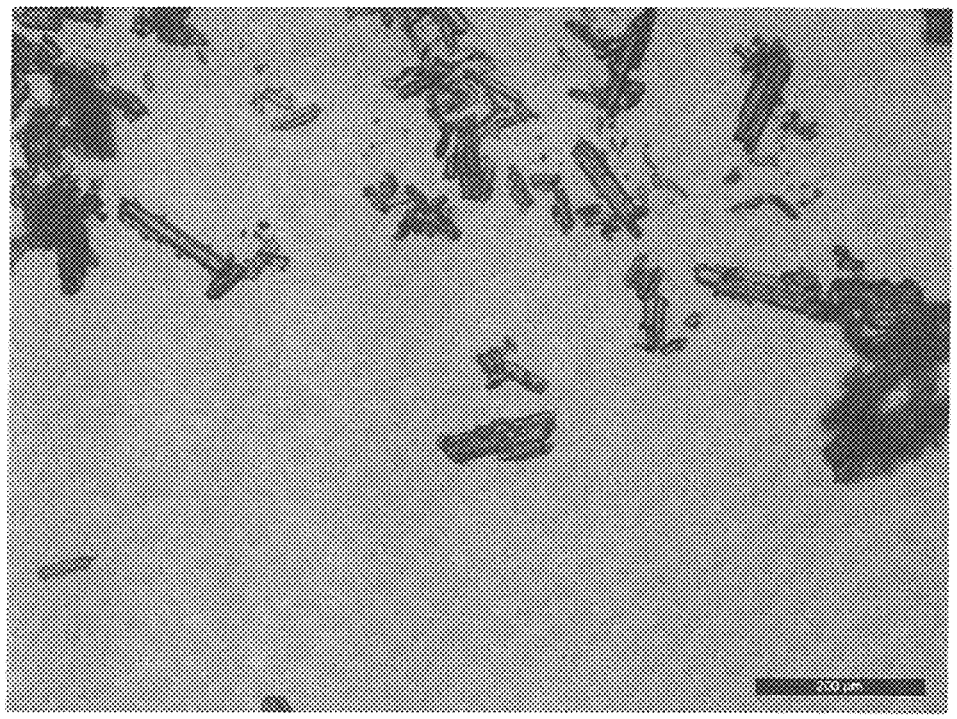
FIG. 22 is a figure showing a photograph of optical microscope of Ra3 type crystal form.
Figure 23:
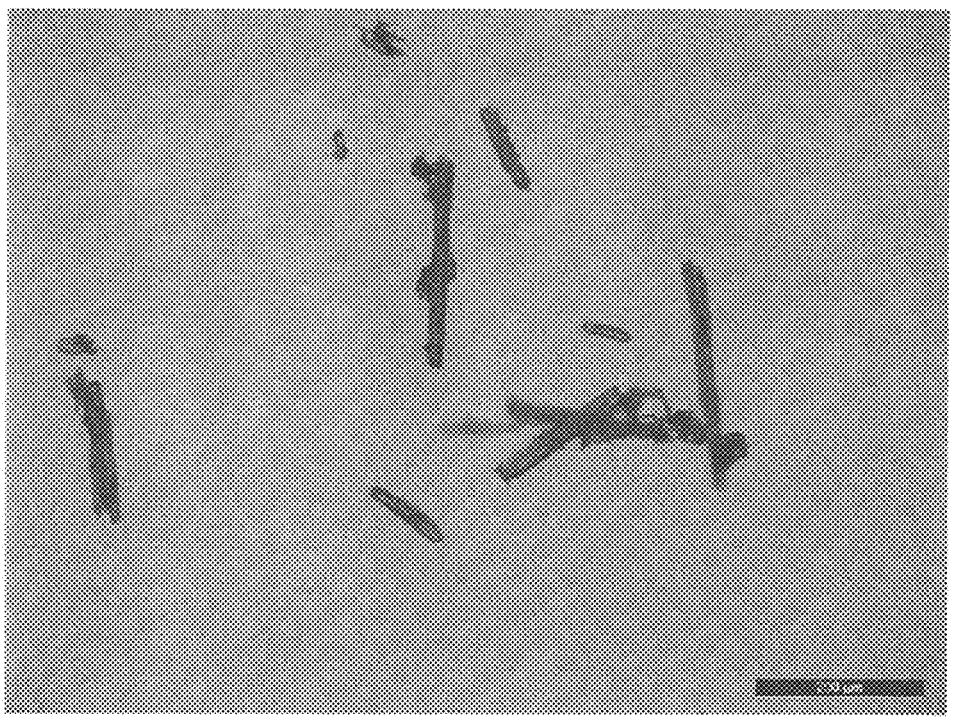
FIG. 23 is a figure showing a photograph of optical microscope of Ra4 type crystal form.

With respect to the characteristic diffraction peak(s) in the powder x-ray diffraction pattern as shown in FIG. 4, the diffraction peak value(s) as a diffraction angle (2θ±0.2°) is indicated in Table 4, which are not limited thereto.

Table 4

TABLE 4

| Peak No. | 2θ(°) | d value [Å] | Relative intensity [%] |
|---|---|---|---|
| 1 | 5.8 ± 0.2 | 15.4 | 2.2 |
| 2 | 7.2 ± 0.2 | 12.3 | 4.2 |
| 3 | 8.6 ± 0.2 | 10.2 | 100 |
| 4 | 13.8 ± 0.2 | 6.4 | 11.9 |
| 5 | 16.3 ± 0.2 | 5.4 | 43.6 |
| 6 | 16.7 ± 0.2 | 5.3 | 7.9 |
| 7 | 17.4 ± 0.2 | 5.1 | 10.0 |
| 8 | 17.7 ± 0.2 | 5.0 | 2.0 |
| 9 | 19.4 ± 0.2 | 4.6 | 13.6 |
| 10 | 19.8 ± 0.2 | 4.5 | 7.7 |
| 11 | 20.7 ± 0.2 | 4.3 | 19.2 |

Typical examples of the diffraction peaks include 5.8±0.2, 7.2±0.2, 8.6±0.2, 13.8±0.2, 16.3±0.2, 16.7±0.2, 17.4±0.2, 17.7±0.2, 19.5±0.2, 19.8±0.2 and 20.7±0.2 as indicated in Table 4.

The crystallographic data of the single crystal of the present crystal is indicated in Table 5 below.

Table 5

TABLE 5

| | Crystal system | | |
|---|---|---|---|
| | Ra1 type crystal | Ra2 type crystal | Ra3 type crystal |
| T | Room temperature | Room temperature | 100K |
| Class | Monoclinic | Triclinic | Orthorhombic |
| Space group | $P2_1/n$ | $P\bar{1}$ | Pbca |

TABLE 5-continued

| | Crystal system | | |
|---|---|---|---|
| | Ra1 type crystal | Ra2 type crystal | Ra3 type crystal |
| a[Å] | 11.8154(7) | 8.7948(4) | 13.3682(2) |
| b[Å] | 15.9252(10) | 10.2571(4) | 10.22030(10) |
| c[Å] | 19.2480(13) | 21.2271(10) | 49.4319(6) |
| α[°] | 90 | 96.235(7) | 90 |
| β[°] | 92.572(7) | 98.626(7) | 90 |
| γ[°] | 90 | 109.313(8) | 90 |
| Unit Cell volume (Volume V[Å³]) | 3618.11 | 1760.80(17) | 6753.73 |
| Number of molecules in Unit Cell (Z) | 8 | 4 | 16 |
| Density (calculated)[g/cm³] | 1.224 | 1.257 | 1.311 |

The control efficacy of the present crystal against plant diseases was measured by the Test Examples below.

TEST EXAMPLE 1

Each of 5 parts of the Ra1 type crystal form, or the Ra4 type crystal form as comparison control, 35 parts of a mixture of white carbon and ammonium polyoxyethylene alkyl ether sulfate (weight ratio is 1:1) and 60 parts of water were mixed, and the mixture was then finely-ground by a wet grinding method to obtain a formulation. Water was then added to the formulation so as to be 2 ppm as the concentration of the Ra1 type crystal form or the Ra4 type crystal form to obtain dilutions respectively.

Each of plastic pots was filled with soil and thereto soybean (cv; Kurosengoku) seeds were sown and the soybeans were grown in a greenhouse for 15 days. Thereafter, an aqueous suspension of spores of soybean rust fungus (*Phakopsora pachyrhizi*) was spraying-inoculated. After the inoculation, the soybeans were placed under a dark and wet condition at 23° C. for 1 night and were further cultivated in a greenhouse for 3 days, and the above-mentioned diluted dilutions were sprayed to foliar parts so as to adhere adequately on the leaves of the above-mentioned soybean. After spraying the dilutions, the plants were air-dried and were placed under a dark and wet condition at only night, and after 7 days of the spraying, the lesion area was observed (lesion area in treated group).

Whereas, in the untreated group, the similar procedures to those of the treated group except that the Ra1 type crystal form or the Ra4 type crystal form were not applied, were carried out and the lesion area of soybean rust disease in the untreated group was observed (lesion area in untreated group).

From each of the lesion area in the treated group or the untreated group respectively, the efficacy in the treated group was calculated by the following "Equation 1". The test results are indicated in Table 6.

$$\text{Efficacy (\%)}=[1-(\text{lesion area in the treated group}/\text{lesion area in the untreated group})]\times 100 \quad \text{[Equation 1]}$$

Table 6

TABLE 6

| Testing crystals | Efficacy (%) |
|---|---|
| Ra1 type crystal form | 72 |
| Ra4 type crystal form | 54 |

It was found that the Ra1 type crystal form showed higher efficacy compared to the Ra4 type crystal form.

TEST EXAMPLE 2

Each of 5 parts of the Ra2 type crystal form, the Ra3 type crystal form, the Ra4 type crystal form as comparison control, 35 parts of a mixture of white carbon and ammonium polyoxyethylene alkyl ether sulfate (weight ratio is 1:1) and 60 parts of water were mixed, and the mixture was then finely-ground by a wet grinding method to obtain a formulation. Water was then added to the formulation so as to be 50 ppm as the concentration of the Ra2 type crystal form, the Ra3 type crystal form, or the Ra4 type crystal form to obtain dilutions respectively.

Each of plastic pots was filled with soil and thereto rice plant (cv; Hinohikari) seeds were sown and the rice plants were grown in a greenhouse for 17 days. The above-mentioned dilutions were sprayed to foliar parts so as to adhere adequately on the leaves of the above-mentioned rice plants. After spraying the dilutions, the plants were air-dried and were cultivated outdoor for 8 days. Thereafter, the rice plants treated with the above-mentioned spraying and the rice plants infected with blast fungus (*Pyricularia oryzae*) were placed for 11 days while contacting each other, and the lesion area of the treated rice plants was observed (lesion area in treated group).

Whereas, in the untreated group, the similar procedures to those of the treated group except that the Ra2 type crystal form, the Ra3 type crystal form, or the Ra4 type crystal form were not applied, were carried out and the lesion area of rice blast disease in the untreated group was observed (lesion area in untreated group).

From each of the lesion area in the treated group or the untreated group respectively, the efficacy in the treated group was calculated by the above "Equation 1" The test results are indicated in Table 7.

TABLE 7

| Testing crystals | Efficacy (%) |
|---|---|
| Ra2 type crystal form | 85 |
| Ra3 type crystal form | 75 |
| Ra4 type crystal form | 50 |

It was found that the Ra2 type crystal form and the Ra3 type crystal form showed higher efficacy compared to the Ra4 type crystal form.

INDUSTRIAL APPLICABILITY

The present crystals (the Ra1 type crystal form, the Ra2 type crystal form, and the Ra3 type crystal form) show an excellent control efficacy against plant diseases.

The invention claimed is:

1. A racemic crystal of 3-(difluoromethyl)-1-methyl-N-(1,1,3-trimethyl-2,3-dihydro-1H-inden-4-yl)-1H-pyrazole-4-carboxamide, which is selected from at least one of a group consisting of
   a Ra1 type crystal form which in a powder x-ray diffraction due to Cu-Kα radiation, has a diffraction peaks $2\theta$ of 7.1±0.2°, 8.6±0.2°, 8.9±0.2°, 9.1±0.2°, 13.3±0.2°, 14.0±0.2°, 14.3±0.2°, 14.8±0.2°, 16.0±0.2°, 16.4±0.2°, 20.3±0.2°, and 20.6±0.2°,
   a Ra2 type crystal form which in a powder x-ray diffraction due to Cu-Kα radiation, has a diffraction peaks $2\theta$ of 4.3=0.2°, 8.5±0.2°, 10.8±0.2°, 11.4±0.2°, 12.4±0.2°, 12.8=0.2°, 15.1±0.2°, 16.1±0.2°, 16.8±0.2°, and 19.1±0.2°, and
   a Ra3 type crystal form which in a powder x-ray diffraction due to Cu-Kα radiation, has a diffraction peaks $2\theta$ of 3.6±0.2°, 7.1±0.2°, 7.4±0.2°, 9.6±0.2°, 11.9-0.2°, 12.5±0.2°, 12.9±0.2°, 14.3±0.2°, 15.7±0.2°, and 17.9±0.2°.

2. The racemic crystal of 3-(difluoromethyl)-1-methyl-N-(1,1,3-trimethyl-2,3-dihydro-1H-inden-4-yl)-1H-pyrazole-4-carboxamide according to claim 1, which is a Ra1 type crystal form which in a powder x-ray diffraction due to Cu-Kα radiation, has a diffraction peaks $2\theta$ of 7.1±0.2°, 8.6=0.2°, 8.9±0.2°, 9.1±0.2°, 13.3=0.2°, 14.0±0.2°, 14.3=0.2°, 14.8=0.2°, 16.0±0.2°, 16.4±0.2°, 20.3±0.2°, and 20.6=0.2°.

3. The racemic crystal of 3-(difluoromethyl)-1-methyl-N-(1,1,3-trimethyl-2,3-dihydro-1H-inden-4-yl)-1H-pyrazole-4-carboxamide according to claim 1, which is a Ra2 type crystal form which in a powder x-ray diffraction due to Cu-Kα radiation, has a diffraction peaks $2\theta$ of 4.3±0.2°, 8.5±0.2°, 10.8±0.2°, 11.4±0.2°, 12.4±0.2°, 12.8±0.2°, 15.1=0.2°, 16.1±0.2°, 16.8±0.2°, and 19.1=0.2°.

4. The racemic crystal of 3-(difluoromethyl)-1-methyl-N-(1,1,3-trimethyl-2,3-dihydro-1H-inden-4-yl)-1H-pyrazole-4-carboxamide according to claim 1, which is a Ra3 type crystal form which in a powder x-ray diffraction due to Cu-Kα radiation, has a diffraction peaks $2\theta$ of 3.6=0.2°, 7.1±0.2°, 7.4±0.2°, 9.6±0.2°, 11.9=0.2°, 12.5=0.2°, 12.9±0.2°, 14.3±0.2°, 15.7=0.2°, and 17.9±0.2°.

5. A composition for controlling a plant disease comprising one or more crystals according to claim 1.

6. A method for controlling a plant disease which comprises applying an effective amount of one or more crystals according to claim 1 to a plant or a soil where the plant grows.

7. A composition comprising one or more crystals according to claim 1 and one or more additional ingredients selected from the group consisting of insecticides, miticides, nematicides, fungicides, plant growth regulators and repellents.

8. A seed or vegetative reproductive organ carrying an effective amount of one or more crystals according to claim 1.

9. A seed or vegetative reproductive organ carrying an effective amount of the composition according to claim 5.

* * * * *